United States Patent
Park, IV et al.

(10) Patent No.: US 10,685,091 B1
(45) Date of Patent: Jun. 16, 2020

(54) SYSTEM AND METHOD FOR DISPENSING PHARMACEUTICAL DOSES

(71) Applicant: PharmRight Corporation, Charleston, SC (US)

(72) Inventors: William C Park, IV, Charleston, SC (US); Jan Pfister Park, Charleston, SC (US)

(73) Assignee: PharmRight Corporation, Charleston, SC (US)

( * ) Notice: Subject to any disclaimer, the term of this patent is extended or adjusted under 35 U.S.C. 154(b) by 434 days.

(21) Appl. No.: 15/423,316

(22) Filed: Feb. 2, 2017

Related U.S. Application Data

(60) Provisional application No. 62/290,265, filed on Feb. 2, 2016.

(51) Int. Cl.
| | | |
|---|---|---|
| *A61J 7/00* | (2006.01) | |
| *G06F 19/00* | (2018.01) | |
| *G08B 21/18* | (2006.01) | |
| *G06K 7/10* | (2006.01) | |

(52) U.S. Cl.
CPC ........ *G06F 19/3462* (2013.01); *A61J 7/0084* (2013.01); *G06K 7/10425* (2013.01); *G08B 21/187* (2013.01); *A61J 2205/60* (2013.01)

(58) Field of Classification Search
CPC .................................................. G07F 17/0092
USPC .............................................. 700/231–244
See application file for complete search history.

(56) References Cited

U.S. PATENT DOCUMENTS

| | | |
|---|---|---|
| 3,722,740 A | 3/1973 | List |
| 4,024,984 A | 5/1977 | Gyimothy et al. |
| 4,223,801 A | 9/1980 | Carlson |
| 4,573,606 A | 3/1986 | Lewis et al. |
| 4,903,861 A | 2/1990 | Yuyama |
| 5,219,095 A | 6/1993 | Shimizu et al. |

(Continued)

OTHER PUBLICATIONS

"Daniel Island Resident Designs Innovative Solution for Managing Meds," The Daniel Island News, Dec. 18, 2013, accessed on Apr. 10, 2018 from http://thedanielislandnews.com/di-resident-designs-innovative-solution-managing-meds, all enclosed pages cited.

*Primary Examiner* — Timothy R Waggoner
(74) *Attorney, Agent, or Firm* — Nelson Mullins Riley & Scarborough, LLP

(57) ABSTRACT

A solid dosage dispensing apparatus comprising a user interface including a display. A plurality of containers are provided from which solid dosages are dispensed. The apparatus includes a controller operative during a stocking mode to: (i) present on said display a list of different solid dosage types available for stocking; (ii) receive an indication of a selected solid dosage type; (iii) graphically indicate on the display a container location at which the selected dosage type is to be located; and (iv) confirm container removal from the container location and subsequent container replacement in that location. During a travel pack mode, the controller is operative to: (i) present on said display a prompt to indicate a duration for which a travel pack is to be stocked; (ii) receive an indication of the duration; and (iii) cause dispensing of dosage types for the duration that would otherwise be dispensed by said apparatus as they are to be administered. In some preferred embodiments, the solid dosage dispensing apparatus may include a readable indicia reader such as a RFID unit.

13 Claims, 37 Drawing Sheets

(56) References Cited

U.S. PATENT DOCUMENTS

| | | | |
|---|---|---|---|
| 5,259,532 A | 11/1993 | Schwarzli | |
| 5,323,929 A | 6/1994 | Marlar | |
| 5,337,919 A | 8/1994 | Spaulding et al. | |
| 5,667,096 A | 9/1997 | Wu | |
| 5,671,592 A * | 9/1997 | Yuyama | G07F 17/0092 53/493 |
| 5,765,606 A | 6/1998 | Takemasa et al. | |
| 5,803,309 A | 9/1998 | Yuyama et al. | |
| 5,865,342 A | 2/1999 | Ito et al. | |
| 5,897,024 A | 4/1999 | Coughlin et al. | |
| 5,905,653 A * | 5/1999 | Higham | G07F 17/0092 312/215 |
| 6,073,799 A | 6/2000 | Yuyama et al. | |
| 6,085,938 A | 7/2000 | Coughlin | |
| 6,145,697 A | 11/2000 | Gudish | |
| 6,294,999 B1 * | 9/2001 | Yarin | A61J 7/0481 340/573.1 |
| 6,343,711 B1 | 2/2002 | Coughlin | |
| 6,431,399 B2 | 8/2002 | Gabel et al. | |
| 6,497,342 B2 | 12/2002 | Zhang et al. | |
| 6,659,304 B2 | 12/2003 | Geltser et al. | |
| 6,799,413 B2 | 10/2004 | Aylward | |
| 6,975,922 B2 * | 12/2005 | Duncan | G07F 11/60 700/242 |
| 7,014,063 B2 | 3/2006 | Shows et al. | |
| 7,080,755 B2 | 7/2006 | Handfield et al. | |
| 7,100,792 B2 | 9/2006 | Hunter et al. | |
| 7,118,007 B1 * | 10/2006 | Yates | A61J 7/0481 221/9 |
| 7,249,688 B2 | 7/2007 | Hunter et al. | |
| 7,255,247 B2 | 8/2007 | Aylward | |
| 7,258,249 B1 * | 8/2007 | Frederick | A61G 12/001 221/282 |
| 7,359,765 B2 | 4/2008 | Varvarelis et al. | |
| 7,510,099 B2 | 3/2009 | Knoth et al. | |
| 7,588,167 B2 | 9/2009 | Hunter et al. | |
| 7,669,733 B2 | 3/2010 | Kim | |
| 7,735,683 B2 | 6/2010 | Handfield et al. | |
| 7,747,345 B2 | 6/2010 | Ohmura et al. | |
| 7,747,347 B2 | 6/2010 | Park, IV | |
| 7,789,267 B2 | 9/2010 | Hutchinson et al. | |
| 7,831,334 B2 | 11/2010 | Vollm et al. | |
| 7,952,315 B2 | 5/2011 | Park, IV | |
| 7,988,017 B2 | 8/2011 | Kulberg et al. | |
| 7,991,507 B2 | 8/2011 | Liff et al. | |
| 8,066,150 B2 | 11/2011 | Clarke et al. | |
| 8,108,068 B1 * | 1/2012 | Boucher | A61J 7/0084 700/236 |
| 8,113,849 B2 | 2/2012 | Park, IV | |
| 8,146,331 B2 | 4/2012 | Soloman | |
| 8,234,838 B2 | 8/2012 | Yasunaga et al. | |
| 8,240,506 B2 | 8/2012 | Kulberg et al. | |
| 8,272,534 B2 | 9/2012 | Clarke et al. | |
| 8,386,073 B2 | 2/2013 | Kim | |
| 8,387,343 B2 | 3/2013 | Yasunaga et al. | |
| 8,393,495 B2 | 3/2013 | Kim | |
| 8,887,603 B2 | 11/2014 | Yuyama et al. | |
| 9,550,619 B2 | 1/2017 | Park, IV | |
| 9,770,391 B2 | 9/2017 | Park, IV | |
| 10,369,081 B2 * | 8/2019 | Hines | A61J 7/0418 |
| 2004/0188456 A1 | 9/2004 | Arai et al. | |
| 2007/0145066 A1 | 6/2007 | Knoth et al. | |
| 2008/0099499 A1 | 5/2008 | Kim | |
| 2009/0299522 A1 * | 12/2009 | Savir | A61J 7/0084 700/240 |
| 2013/0018503 A1 * | 1/2013 | Carson | B65B 57/16 700/216 |
| 2013/0256331 A1 | 10/2013 | Giraud et al. | |
| 2014/0310018 A1 * | 10/2014 | Cizmarik | G06F 19/3462 705/2 |
| 2014/0350720 A1 * | 11/2014 | Lehmann | G06F 19/3462 700/236 |
| 2015/0090733 A1 | 4/2015 | Park | |
| 2016/0015602 A1 * | 1/2016 | Panzini | A61J 7/0454 340/666 |
| 2017/0079884 A1 | 3/2017 | Park, IV | |
| 2017/0333290 A1 | 11/2017 | Park, IV | |

\* cited by examiner

SYSTEM AND METHOD FOR DISPENSING PHARMACEUTICAL DOSES

PRIORITY CLAIM

This application is based upon and claims the benefit of U.S. provisional application Ser. No. 62/290,265, filed Feb. 2, 2016, which is incorporated herein by reference in its entirety.

BACKGROUND OF THE INVENTION

This invention relates to automated or on-demand dispensing of medicine, such as for an individual patient.

Many people take more than one medicine or dietary supplement on a periodic basis. Each medicine or dietary supplement may have its own rules for consumption, such as, for example, the frequency, the time of day, and the accompanying food or beverage (or absence thereof). For some people, managing even one once-daily medicine can be challenging: it is possible to forget whether the daily dose has been consumed. When a patient must manage more than one medicine, each with its own rules for consumption, the likelihood for confusion, missed doses, overdose, and general noncompliance by the patient increases. Those problems at best reduce the efficacy of the medicine, and at worst, place the patient at significant risk for untreated illness and drug-related injury.

In-home dosage dispensers have been proposed in the past. Oftentimes, the procedure for operating these dispensers is not intuitive, leading to difficulties in use. These difficulties may be exacerbated by the patient's advanced age or medical condition. Typically, the dispensers are refilled by a patient's caregiver, but the refilling process may itself be difficult or error-prone. Moreover, patients on a pharmaceutical regimen may often leave home on a temporary basis, which is difficult to synchronize with the programmed operation of an automatic dispenser.

The present invention recognizes the foregoing considerations, and others, of the prior art.

SUMMARY OF THE INVENTION

In accordance with one aspect, the present invention provides a solid dosage dispensing apparatus comprising a user interface including a display. A plurality of containers are provided from which solid dosages are dispensed. The apparatus includes a controller operative during a stocking mode to: (i) present on the display a list of different solid dosage types available for stocking; (ii) receive an indication of a selected solid dosage type; (iii) graphically indicate on the display a container location at which the selected dosage type is to be located; and (iii) confirm container removal from the container location and subsequent container replacement in that location.

In some preferred embodiments, the controller is further operative to provide an alarm if a container is placed in an incorrect location. The controller preferably prompts a user to confirm a number of the selected solid dosage type to be added. For example, it is contemplated that the number of the selected solid dosage type can be varied by the user via the user interface.

The apparatus may comprise a lid and the controller may enter the stocking mode upon removal of the lid. In addition, the apparatus may include communication circuitry operative to communicate with a remote host server. For example, the communication circuitry may be operative to communicate with the remote host server via internet connection. Alternatively, the communication circuitry may be operative to communicate with the remote host server via cellular connection. The controller may be operative, for example, to update an inventory of the selected dosage type with the remote host server via the communication circuitry.

In some preferred embodiments, the solid dosage dispensing apparatus may include a readable indicia reader such as a RFID unit.

Another aspect of the present invention provides a solid dosage dispensing apparatus comprising a user interface including a display and a readable indicia reader. A coupling structure configured to mount at least one container from which solid dosages are dispensed is also provided. The apparatus includes a controller operative to: (i) receive information via the readable indicia reader regarding a selected dosage type and the quantity thereof to be stocked; and (ii) confirm that a container has been placed in a selected location on the coupling structure.

A further aspect of the present invention provides a solid dosage dispensing apparatus comprising a user interface including a display. A plurality of containers are provided from which solid dosages are dispensed. The apparatus includes a controller operative during a travel pack mode to: (i) present on the display a prompt to indicate a duration for which a travel pack is to be stocked; (ii) receive an indication of the duration; and (iii) cause dispensing of dosage types for the duration that would otherwise be dispensed by the apparatus as they are to be administered.

Various methodology consistent with the disclosure herein is also provided in accordance with the present invention.

Other objects, features and aspects of the present invention are provided by various combinations and subcombinations of the disclosed elements, as well as methods of practicing same, which are discussed in greater detail below.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying drawings, in which.

Figure 1:
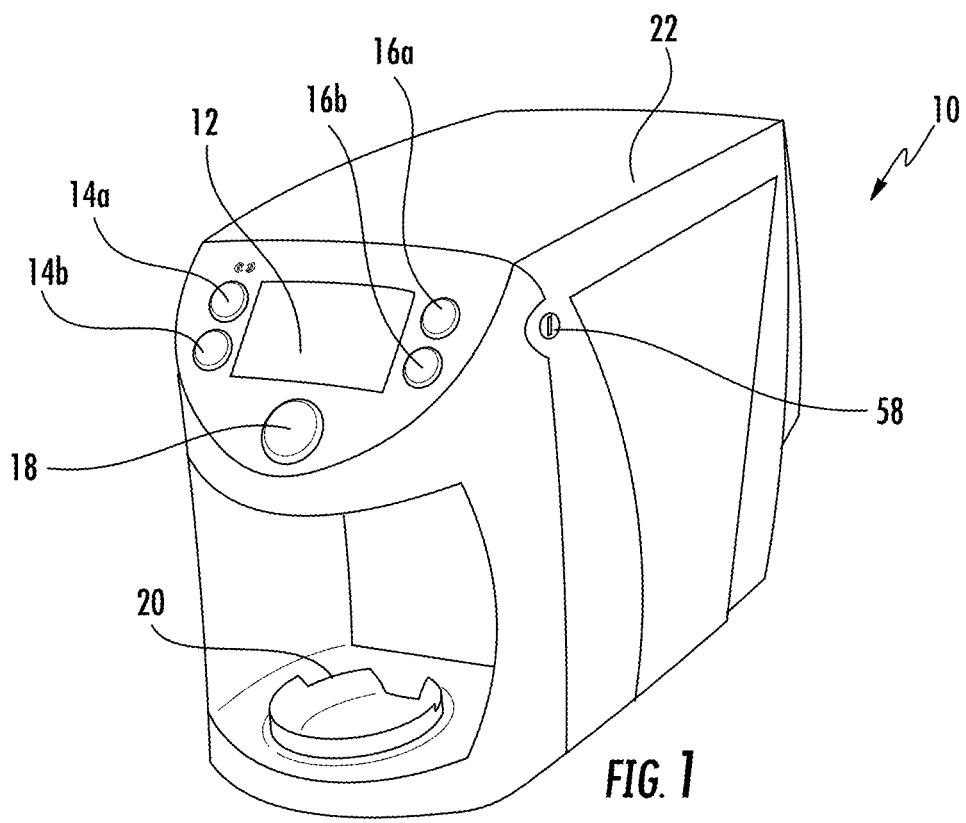
FIG. 1 is a perspective view of a dispensing apparatus in accordance with an embodiment of the present invention.

Repeat use of reference characters in the present specification and drawings is intended to represent same or analogous features or elements of the invention.

DETAILED DESCRIPTION OF PREFERRED EMBODIMENTS

It is to be understood by one of ordinary skill in the art that the present discussion is a description of exemplary embodiments only, and is not intended as limiting the broader aspects of the present invention, which broader aspects are embodied in the exemplary constructions.

Embodiments of the present invention are particularly well-suited for use with a dispenser apparatus as shown and described in U.S. Pub. App. No. 2015/0090733 (now U.S. Pat. No. 9,550,619), incorporated fully herein by reference for all purposes.

Figure 2:
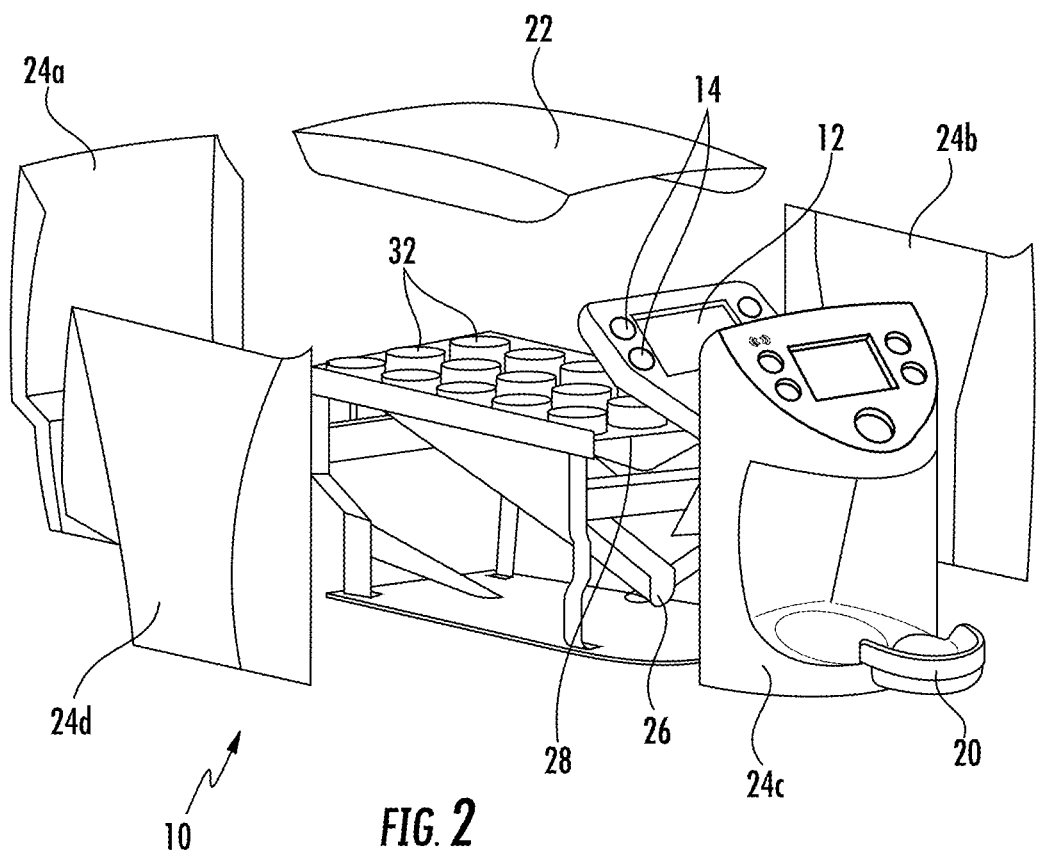
FIG. 2 is an exploded view of the dispensing apparatus of FIG. 1 to reveal certain internal components.
Figure 3:
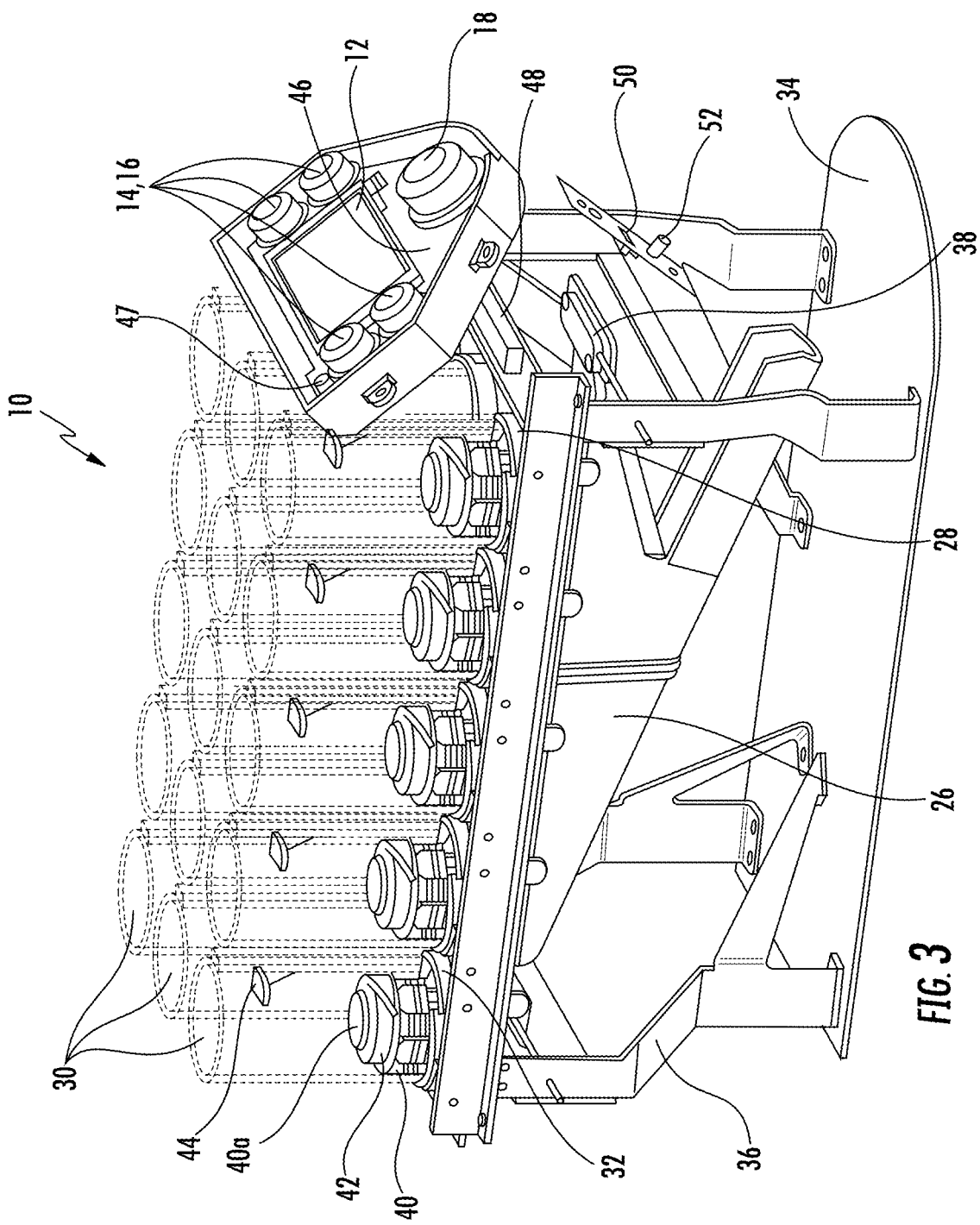
FIG. 3 shows internal components of the dispensing apparatus of FIG. 1 with side panels removed.

Referring first to FIGS. 1 through 3, a dispensing apparatus 10 that practices aspects of the present invention is illustrated. Apparatus 10 includes a housing formed in this embodiment of a plurality of panels. A user interface, located at the front of the housing, includes a display 12 for providing information about the status of apparatus 10, or for displaying selections that can be chosen by a user. The display itself is preferably configured as an LCD color display (or other suitable type of display) having appropriate dimensions.

Buttons 14a-b and 16a-b located on either side of display 12 serve as "soft keys" whose function varies depending on the menu items shown on display 12. For example, buttons 14a-b and 16a-b may be used to scroll among options shown on display 12, or may at times be used to select discrete items shown on display 12. Main button 18 is pressed to dispense a dose at the appropriate time, or may be used in conjunction with the soft keys to select a highlighted item. Preferably, buttons 14, 16, and 18 may illuminate (or have an illuminated surround) that indicates when it is active. When dispensed, the dose drops into dispensing cup 20.

Referring now particularly to FIG. 2, lid 22, body panels 24, and dispensing cup 20 are shown in "exploded" format. In particular, dispensing apparatus 10 has a rear panel 24a, right panel 24b, front panel 24c, and left panel 24d. Doses to be delivered to dispensing cup 20 travel down a dispensing ramp 26 located inside the housing. In this embodiment, dispensing ramp 26 is positioned below the coupling deck 28 to receive solid dosage forms as they emerge from the correct one of storage containers 30 (FIG. 3). Coupling structures 32 allow storage containers 30 to couple removably to the coupling deck 28.

Certain internal components of apparatus can be easily seen in FIG. 3. In this regard, coupling deck 28 is shown elevated above a base 34 via a plurality of support legs (such as leg 36). This provides clearance for the slope of dispensing ramp 26. As noted above, dispensing ramp 26 receives solid dosage forms that emerge from storage containers 30. (For clarity, not all storage containers 30 are labeled.) Preferably, suitable sensor(s), such as fiber optic array 38, are provided to detect passage of the solid dosage form along the ramp 36.

As described in U.S. Pub. App. No. 2015/0090733, a receiver 40 having a convex surface 40a is preferably located in a respective storage container 30. A sweeper 42 and a thumb tab 44 for positioning the sweeper 42 are also preferably provided. Coupling structures 32 removably couple a respective storage container 30 to the coupling deck 28. Menu navigation buttons 14, 16 alongside display 12 and a main button 18 below display 12 are all mounted on a main printed circuit board 46 in this embodiment. The main circuit board may also carry a near field communication (NFC) or RFID unit 47. For example, the patient or authorized user may wear a bracelet having an RFID tag. The patient presents the bracelet to apparatus 10 at the time medicine is to be dispensed for authentication purposes. Unauthenticated users might be prevented from receiving medicine even if the time to dispense the medicine has arrived. Other authentication technologies, including biometrics, might also be used.

Data connector 48 allows for electrical communication between the main printed circuit board 46, on the one hand, and the container printed circuit board attached to the bottom of the coupling deck 28 to selectively activate the motors so as to selectively rotate the receivers 40.

In some preferred embodiment, a microphone 50 is provided to allow a user to respond to audio or visual cues, thereby controlling dispensing apparatus 10 by voice command. Also, microphone 50 can be configured to detect the sound of a solid dosage form emerging from the dispensing ramp 26 and landing in the dispensing cup 20. Furthermore, microphone 50 can be used to allow a user to communicate with a remote health care professional if apparatus 10 is in electrical communication with a network such as the Internet or cellular network. Light 52 can be configured to illuminate the dispensing cup when solid dosage forms are dispensed into the dispensing cup.

Figure 4:
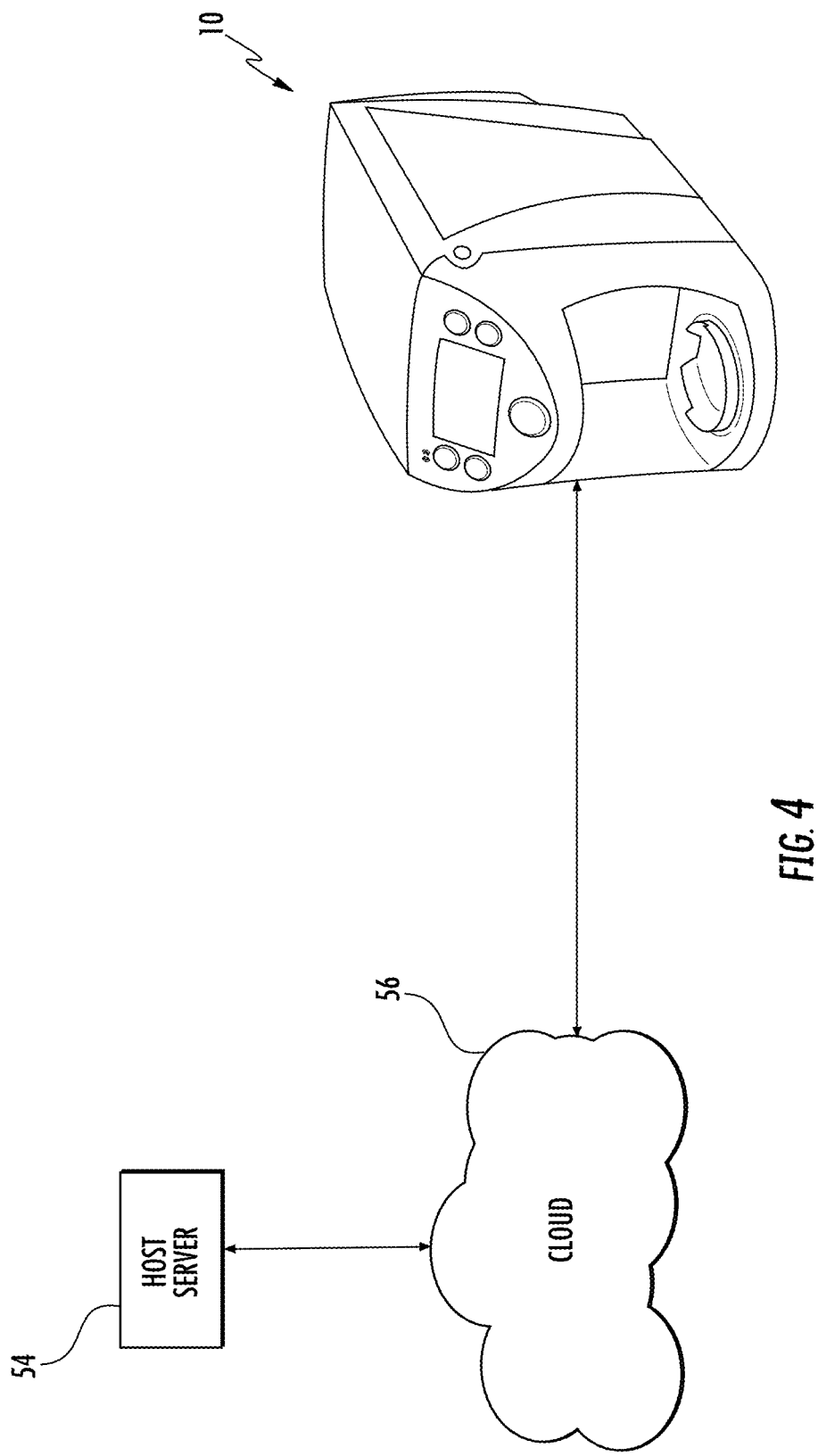
FIG. 4 is a diagrammatic representation showing communication of the dispensing apparatus of FIG. 1 with a host server.

In fact, as shown in FIG. 4, preferred embodiments of apparatus 10 are configured to communicate on at least a periodic basis with a remote host server 54. Any suitable means for effecting such communication may be utilized, although presently preferred embodiments utilize cellular or internet communication. In the illustrated embodiment, for example, apparatus 10 may be part of a local area network (such as a common home network) and communicates with host server 54 via the internet (indicated at 56). In some cases, it may be desirable to provide cellular backup for any internet connection, or a cellular modem located inside of apparatus 10 may be the primary means of communication.

Preferably, host server 54 receives information regarding the status and contents of apparatus 10. In this embodiment, for example, lid 22 can be removed from the housing of apparatus 10 to allow restocking of the dosages contained inside. It is contemplated that the patient should not have access to the inside of apparatus 10, and this restocking would be performed by a caregiver. As a result, a lock 58 is associated with lid 22 to limit unauthorized entry. In addition, however, a notification may be sent by apparatus 10 to host server 54 whenever the lid is removed. Host server 54 can determine if the lid's removal is part of an authorized restocking process. If not, appropriate action can be taken.

In addition, host server 54 can monitor the dosages as they are dispensed so that re-stocking can be planned before the medicine is completely depleted. In addition, prescription changes can be sent to apparatus 10 as they occur to prevent over-dispensing or under-dispensing of the medicines contained therein. For example, if a prescription for a certain medicine is terminated, apparatus 10 can be instructed not to allow any further dispensing of that medicine. Similarly, the dispensing frequency of a particular medicine can be changed to reflect modifications of the prescribed dose.

Figure 5:
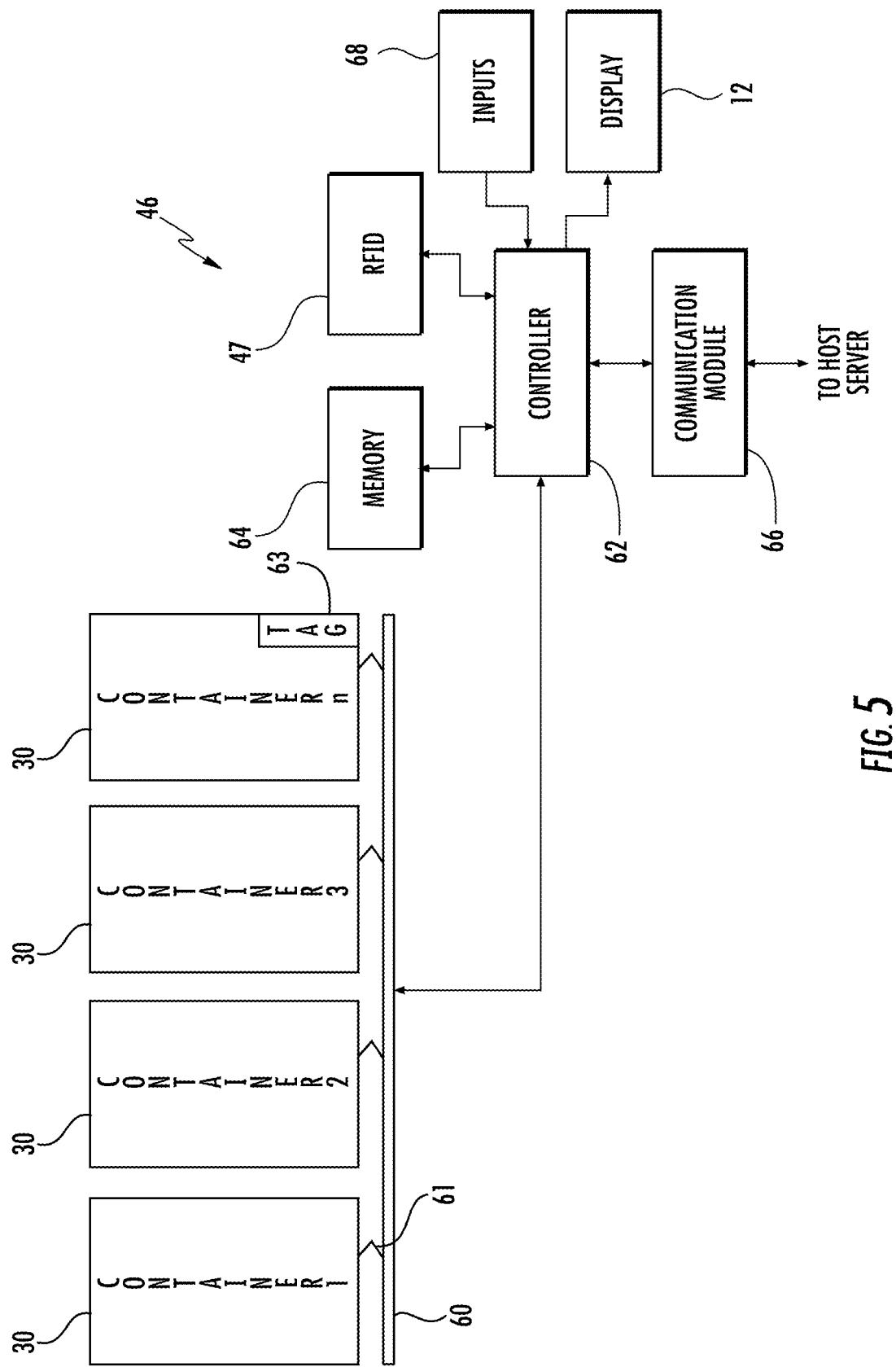
FIG. 5 is a diagrammatic representation showing functional components of the dispensing apparatus of FIG. 1.

Referring now to FIG. 5, a plurality of containers 30 (labeled "container 1" through "container n") are shown located above the container printed circuit board 60. A suitable mechanism, in this case a respective micro-switch 61, is provided to detect whether a container is present in its designated location. Container printed circuit board 60 communicates with a controller 62 located on main printed circuit board 46. In some preferred embodiments, each of the containers 30 may be provided with an RFID tag 63 for reasons to be described below.

As shown, main printed circuit board 46 further includes a memory 64 that communicates with controller 62. Memory 64 preferably comprises both volatile and nonvolatile portions that contain program instructions and allow temporary storage of data during operation. While shown as a single component in FIG. 5, one skilled in the art will appreciate that parts of memory 64 may be distributed over multiple chips. For example, program instructions may be contained on an EEPROM or other nonvolatile memory whereas the "hot memory" may be part of a separate chip. The communication module 66, e.g., a network adapter or cellular modem, provides communication with host server 54 as described above. Inputs (collectively indicated at 68) correspond to buttons 14, 16, and 18 in this embodiment. RFID unit 47 also communicates with controller 62, as shown.

Figure 6:
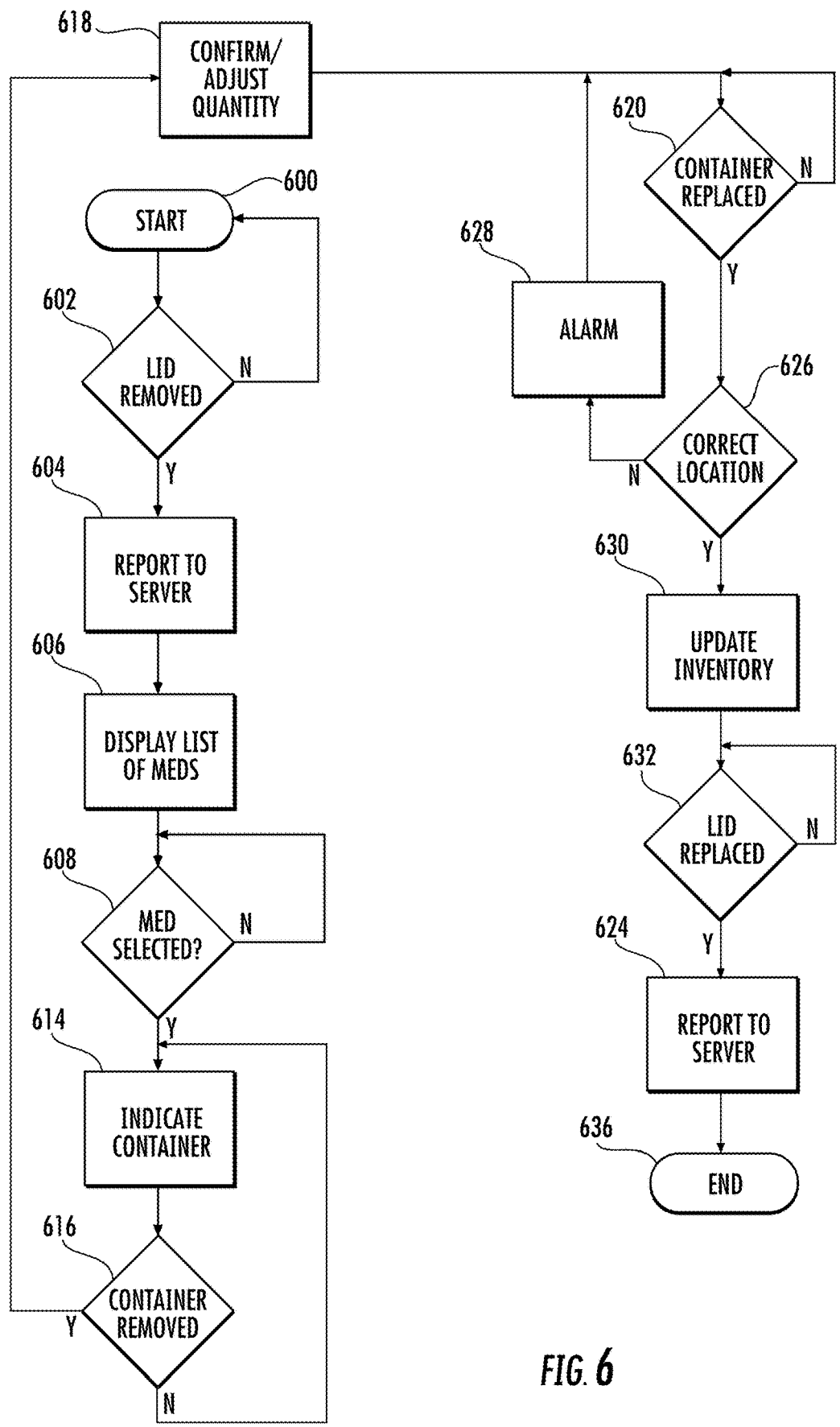
FIG. 6 is a flowchart illustrating an exemplary stocking method that may be employed in the dispensing apparatus of FIG. 1.

Aspects of the present invention provide improved methodology for restocking a dispensing apparatus such as apparatus 10. As will be described, logical rules may be programmed into apparatus 10, host server 54, or both, in order to address certain considerations that may arise in the re-stocking process. Toward this end, FIG. 6 shows exemplary re-stocking methodology in accordance with an embodiment of the present invention. The methodology of FIG. 6 is taken from the perspective of what occurs at apparatus 10, although some functions may be initiated by the caregiver.

The process starts at 600. Apparatus 10 then determines whether lid 22 has been unlocked and/or removed (at 602). If the lid is unlocked (and/or removed), apparatus 10 reports its status (at 604) to host server 54. During periods when the lid is not removed, the process loops back. A list of the contained medicine is shown (at 606) on display 12 so that the appropriate medicine can be selected (at 608).

If the medicine to be stocked has been selected, apparatus 10 shows on display 12 the location of the appropriate container to be removed (at 614). Apparatus 10 then determines whether the correct container has been removed (at 616). If the correct container has been removed, apparatus 10 prompts the user to confirm and/or adjust the refill quantity of the selected medicine (at 618).

Apparatus 10 further prompts the user to replace the container in the correct location. Apparatus 10 determines not only if the container has been replaced (at 620), but confirms that it was replaced in the correct location (at 626). If not, an alarm (e.g., a visual and/or audible alarm) can be generated (at 628) to inform the user of the misplacement. As a result, the user can move the container from the incorrect location to the correct location.

If the container is placed in the correct location, apparatus 10 updates the inventory (at 630) to reflect the refill. Depending on the embodiment, the inventory data may be updated locally in the memory of apparatus 10 and/or uploaded to host server 54. Apparatus 10 then determines (at 632) if the lid has been replaced (and/or locked). The final status is preferably reported to host server 54 (at 624) and the process ends (at 636).

FIGS. 9-20 show an exemplary display sequence that restocking personnel might see on display 12 in accordance with the methodology of FIG. 6. These screen displays are believed to be self-explanatory, when considered in light of the above discussion, and need not be further described.

While FIG. 6 describes a situation where containers of apparatus 10 are being refilled on site, embodiments are contemplated in which containers 30 are consumable items which are discarded when their supply is depleted. In this case, for example, the containers might be filled and sealed in a remote pharmacy and sent to the caregiver to insert into apparatus 10. Thus, FIG. 7 illustrates one preferred alternative where pre-filled containers are used.

Figure 7:
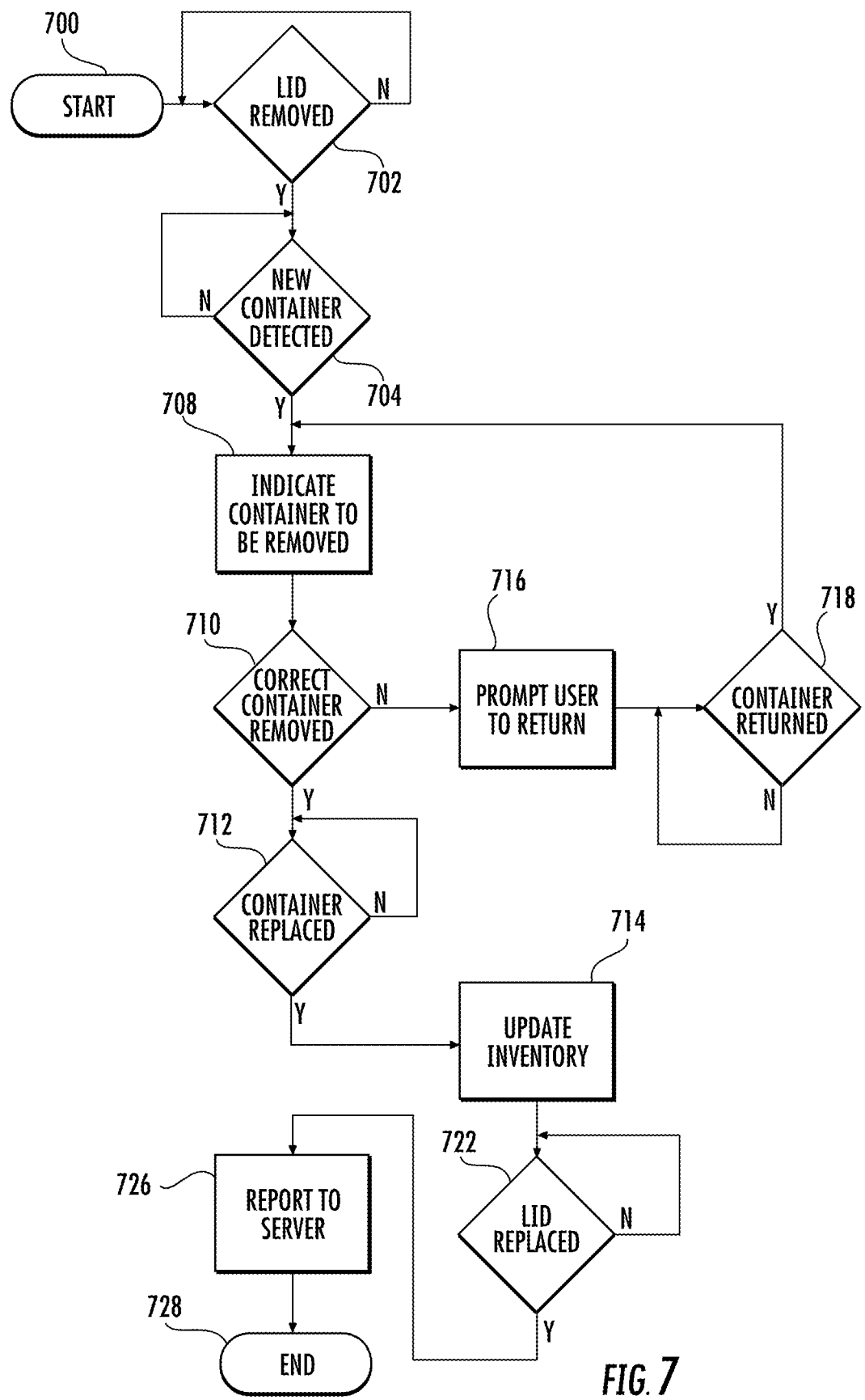
FIG. 7 is a flowchart illustrating another exemplary stocking method that may be employed in the dispensing apparatus of FIG. 1.

Thus, referring to FIG. 7, process begins at 700. Apparatus 10 then determines whether lid 22 has been unlocked and/or removed (at 702). During periods when the lid is not removed, the process loops back. Apparatus 10 then determines whether a pre-filled container is detected (as indicated at 704). For example, the new container 30 may have an RFID tag 63, QR code, or other readable indicia that identifies itself to apparatus 10. As so programmed, the indicia may identify the target apparatus 10, as well as the type and quantity of doses in the container.

If a new pre-filled container is detected, apparatus 10 may "know" from the readable indicia which old container is to be replaced, and so indicate (at 708) on display 12. If the correct container is removed (at 710) and replaced (at 712), the inventory of apparatus 10 can be updated (at 714) as described above in relation to FIG. 6. If the correct container is not removed, apparatus 10 will suitably prompt the user (at 716) to return the one that was removed and this is confirmed (at 718). The process will not continue until the user complies.

After the removed container has been replaced (at 722), apparatus 10 then updates the inventory (at 714) either locally and/or at host server 54. Apparatus 10 then determines (at 722) if the lid has been replaced (and/or locked). The final status is preferably reported to host server 54 (at 726) and the process ends (at 728).

Figure 8:
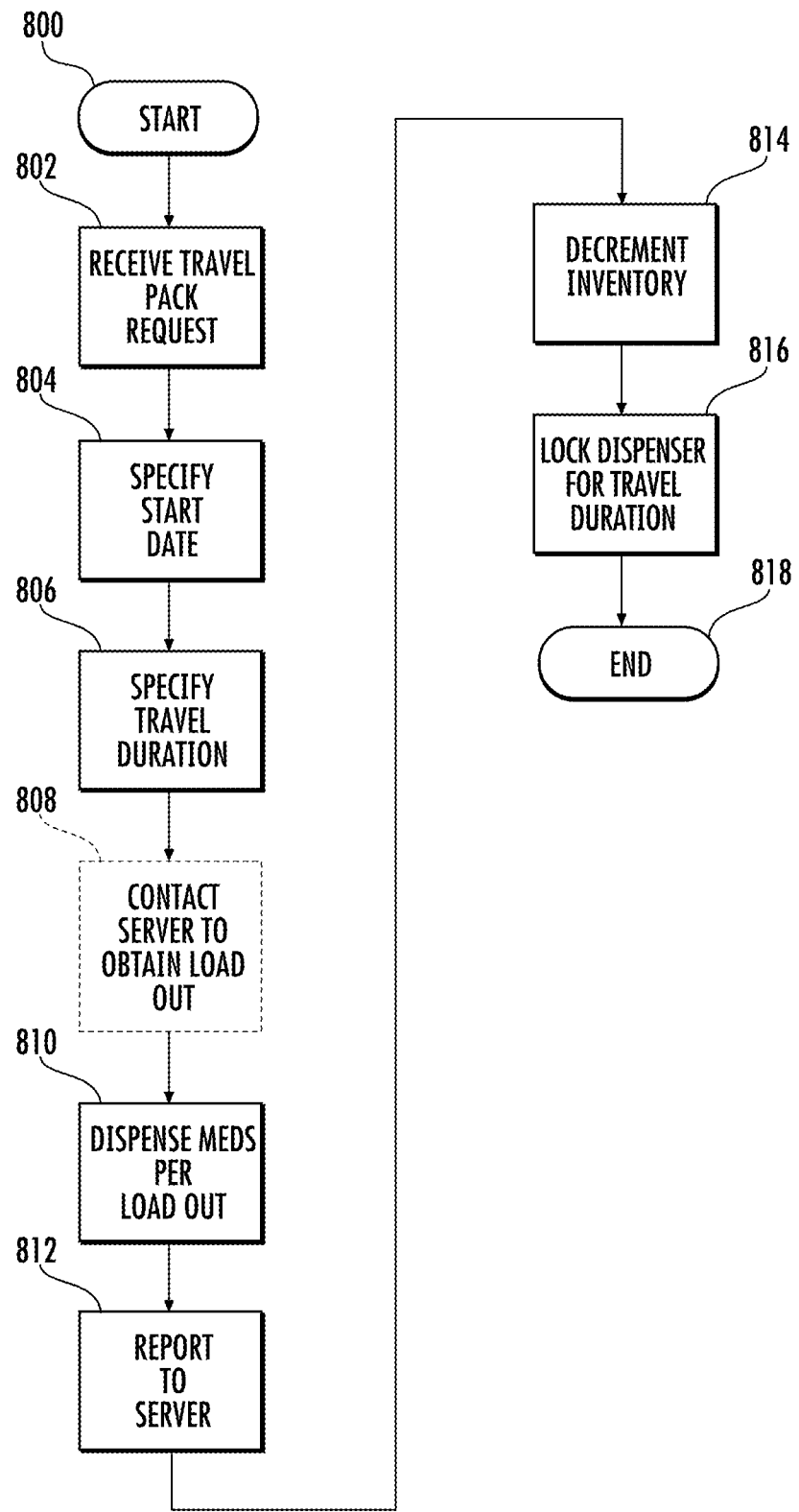
FIG. 8 is a flowchart illustrating an exemplary travel pack dispensing method that may be employed in the dispensing apparatus of FIG. 1.
Figure 9:
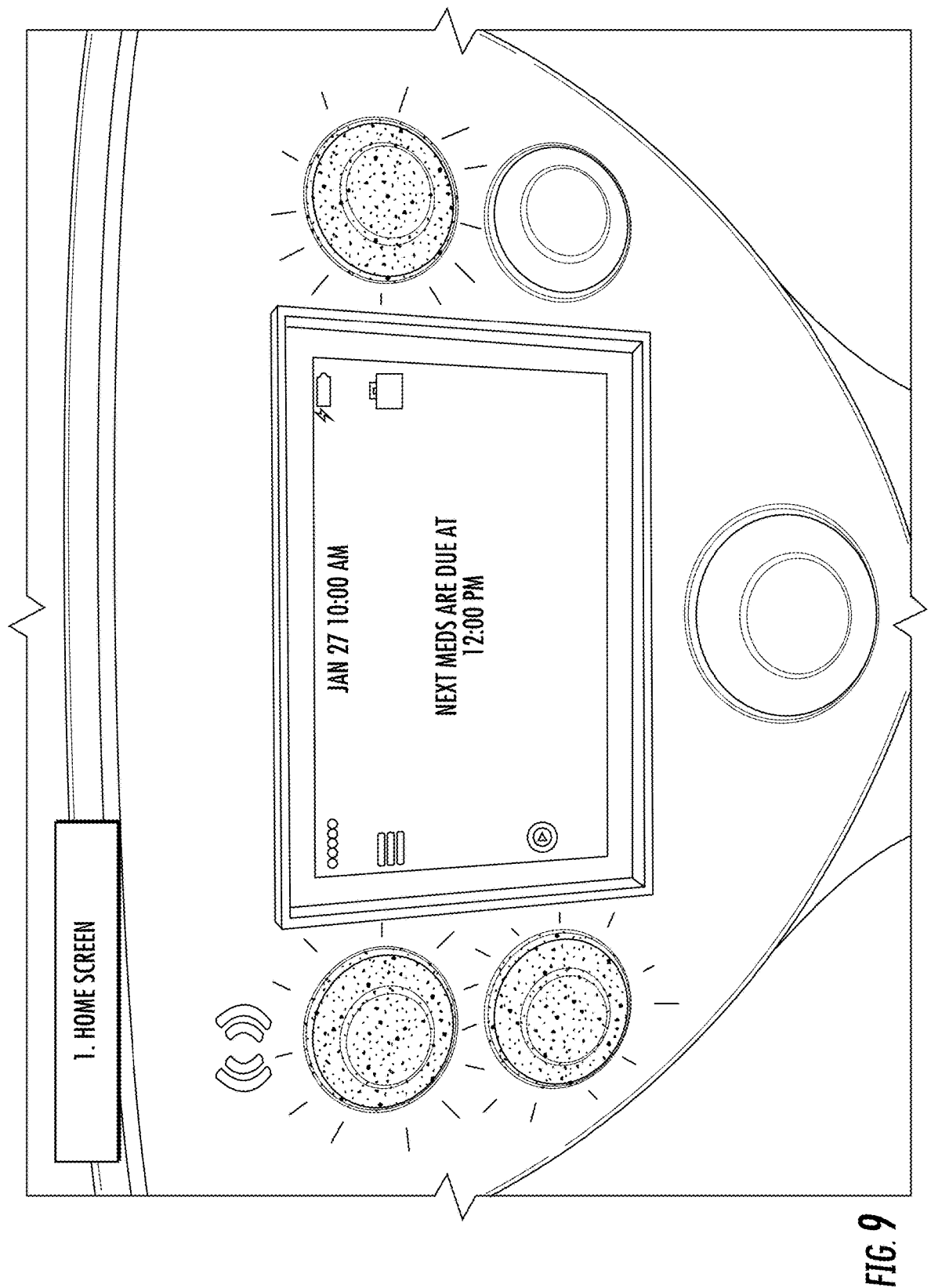
FIGS. 9 through 20 show a display of the dispensing apparatus of FIG. 1 performing a stocking method in accordance with FIG. 6, with illuminated buttons in various of the figures being shown by rays and stippling.
Figure 10:
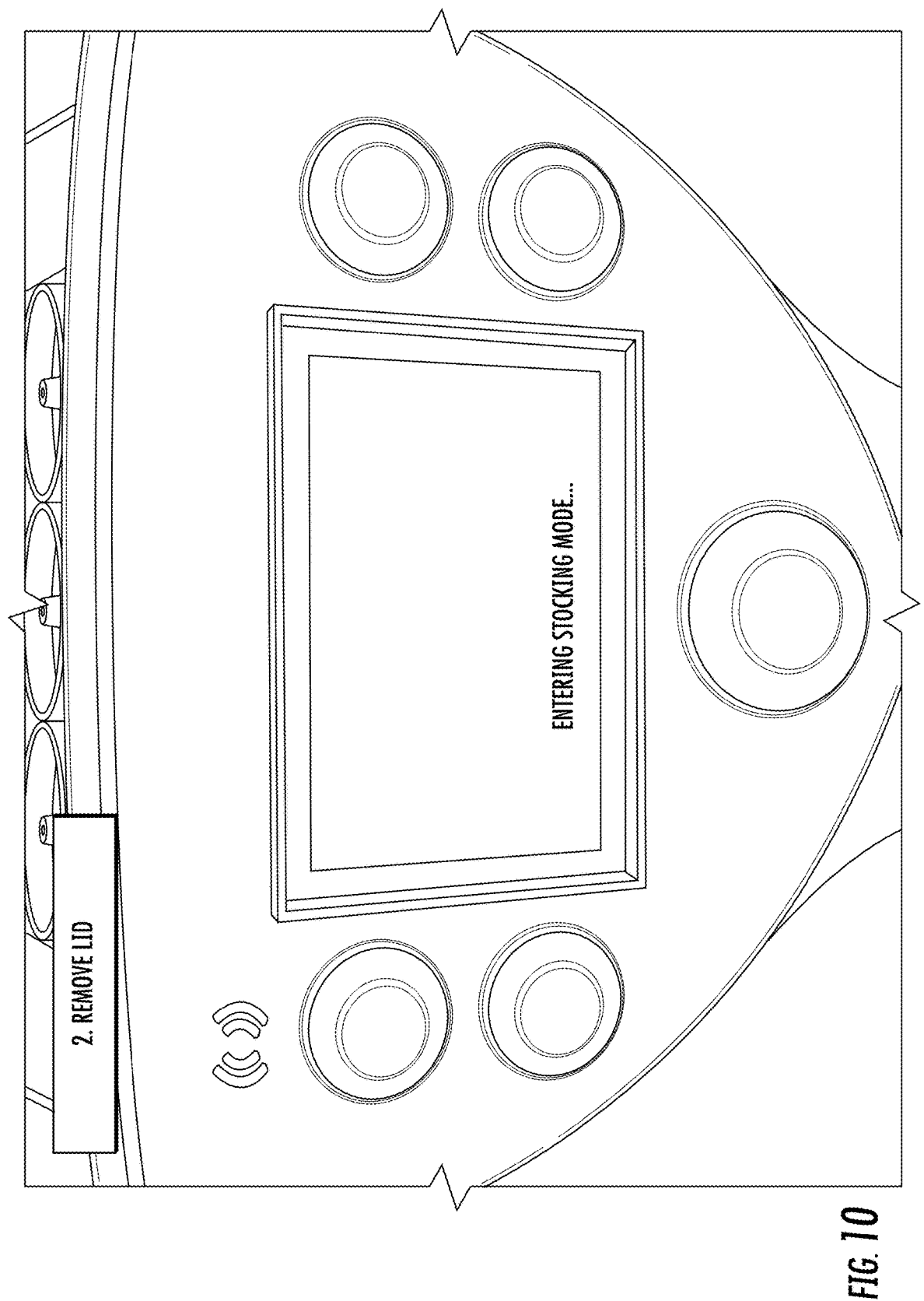
Figure 11:
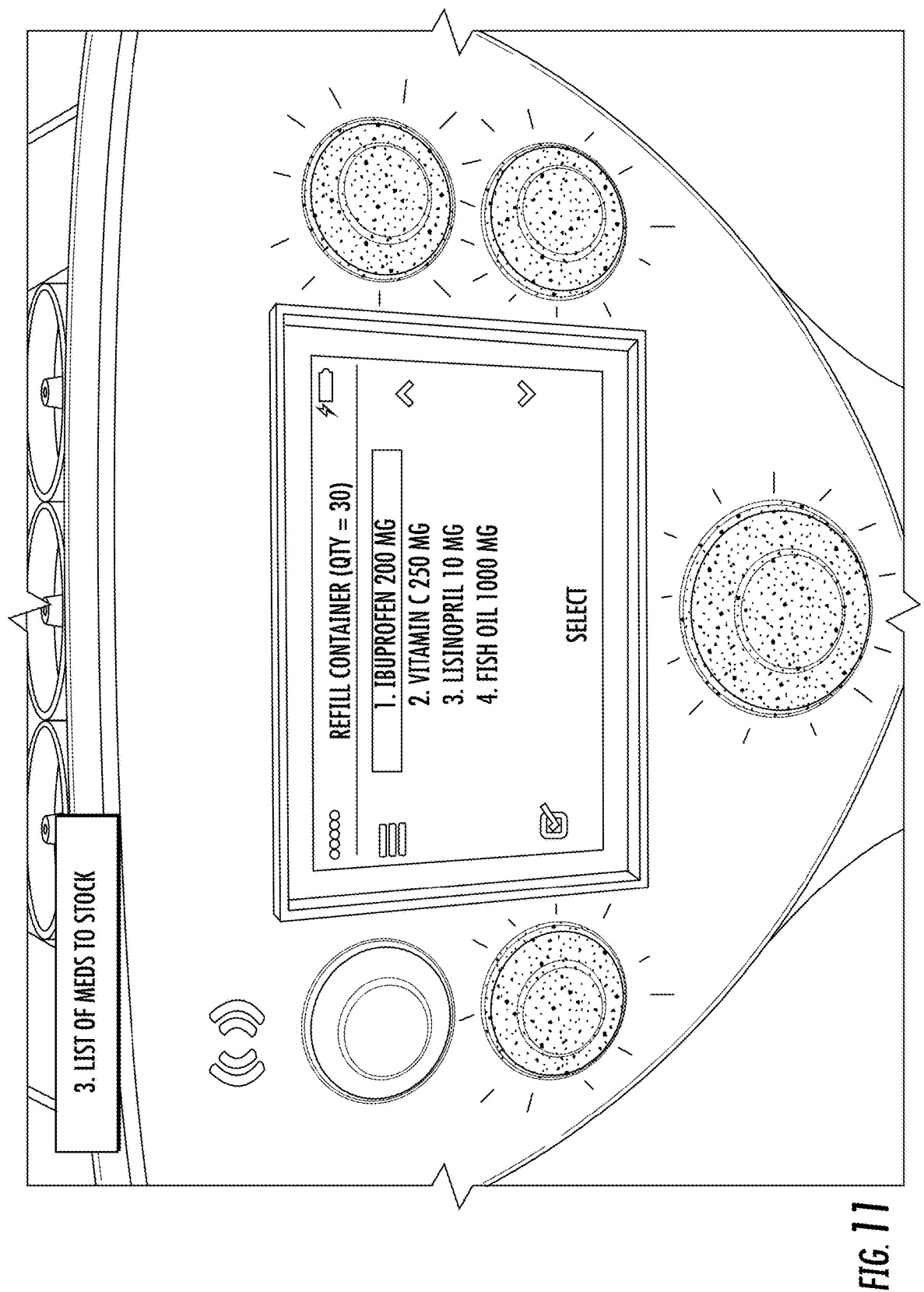
Figure 12:
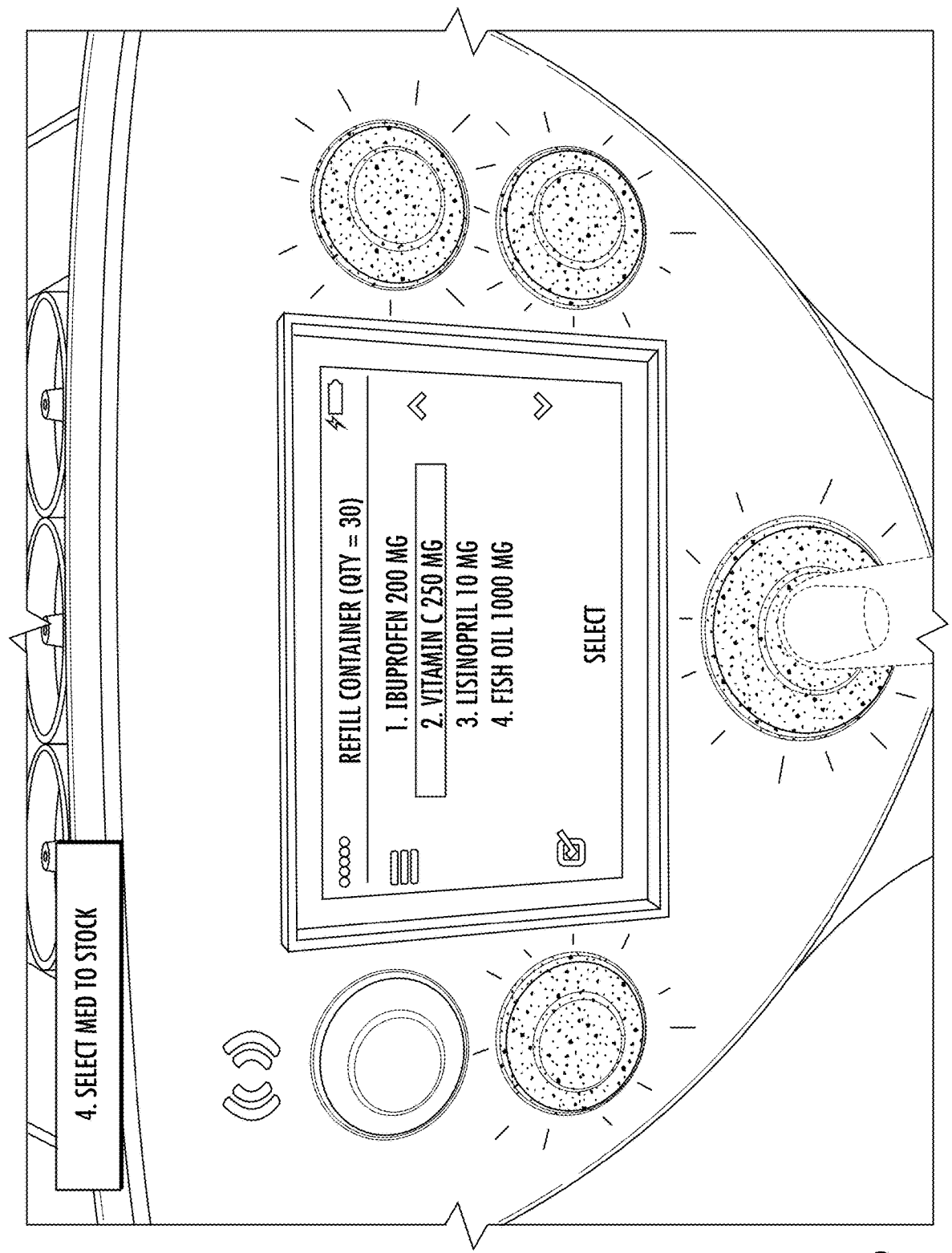
Figure 13:
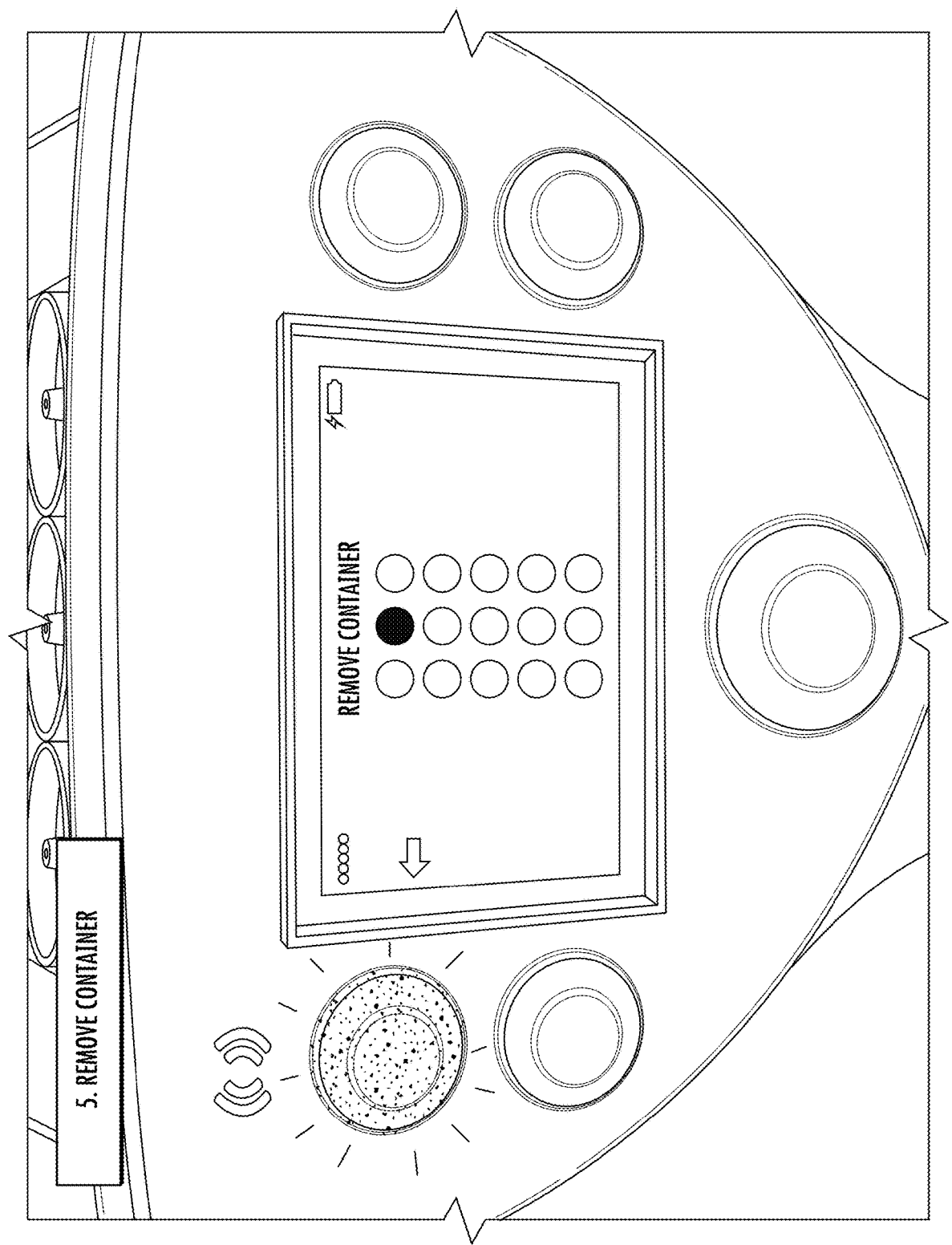
Figure 14:
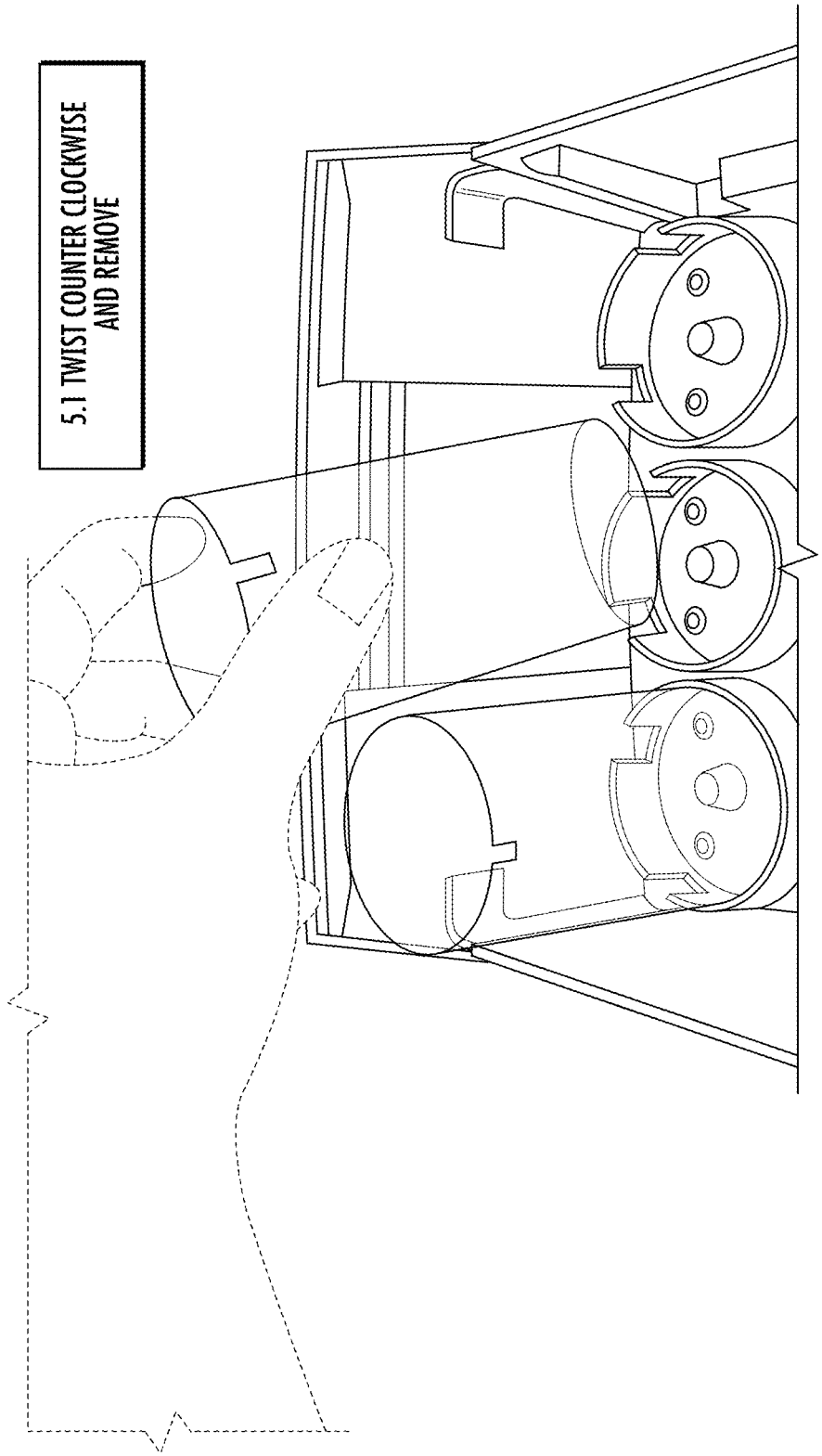
Figure 15:
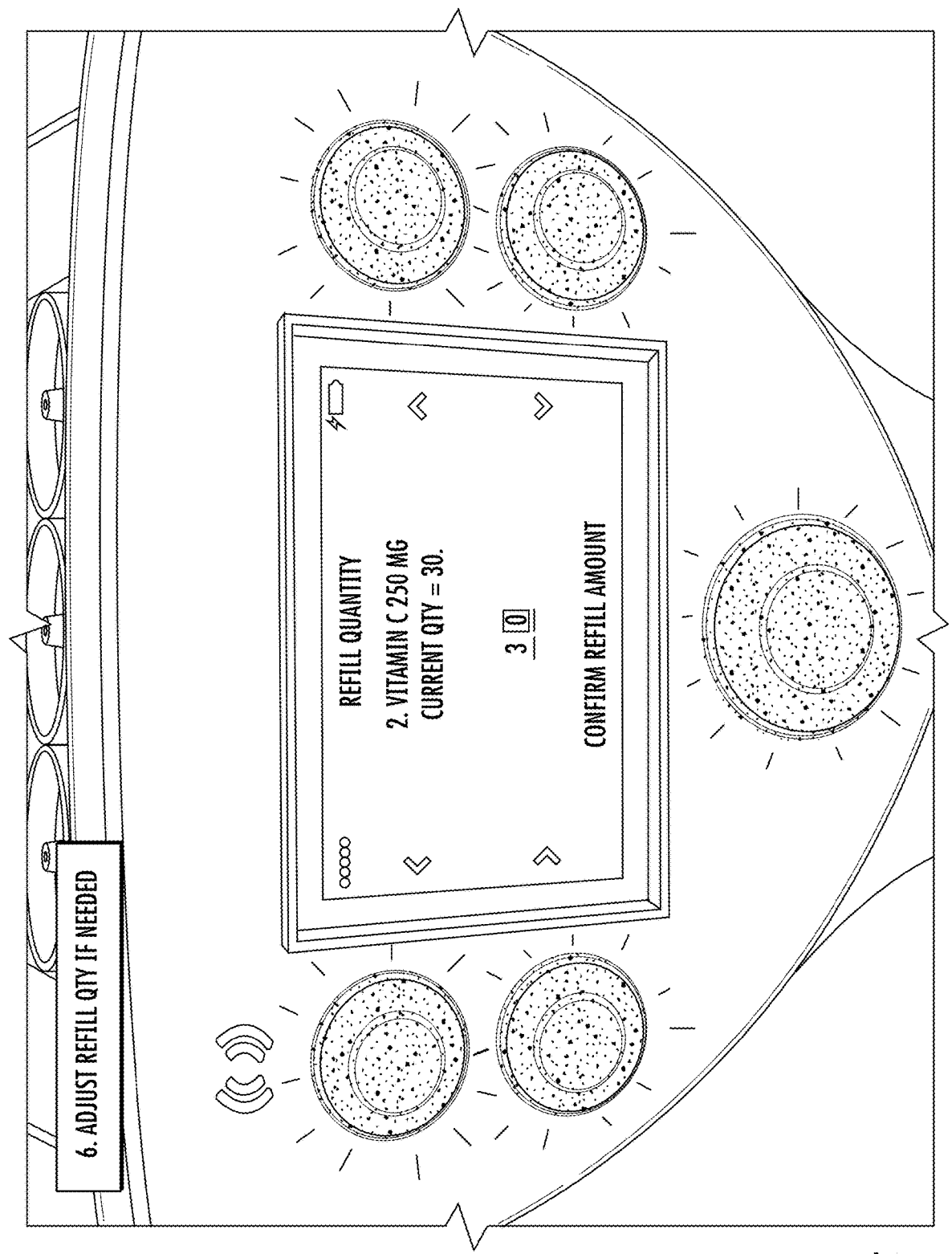
Figure 16:
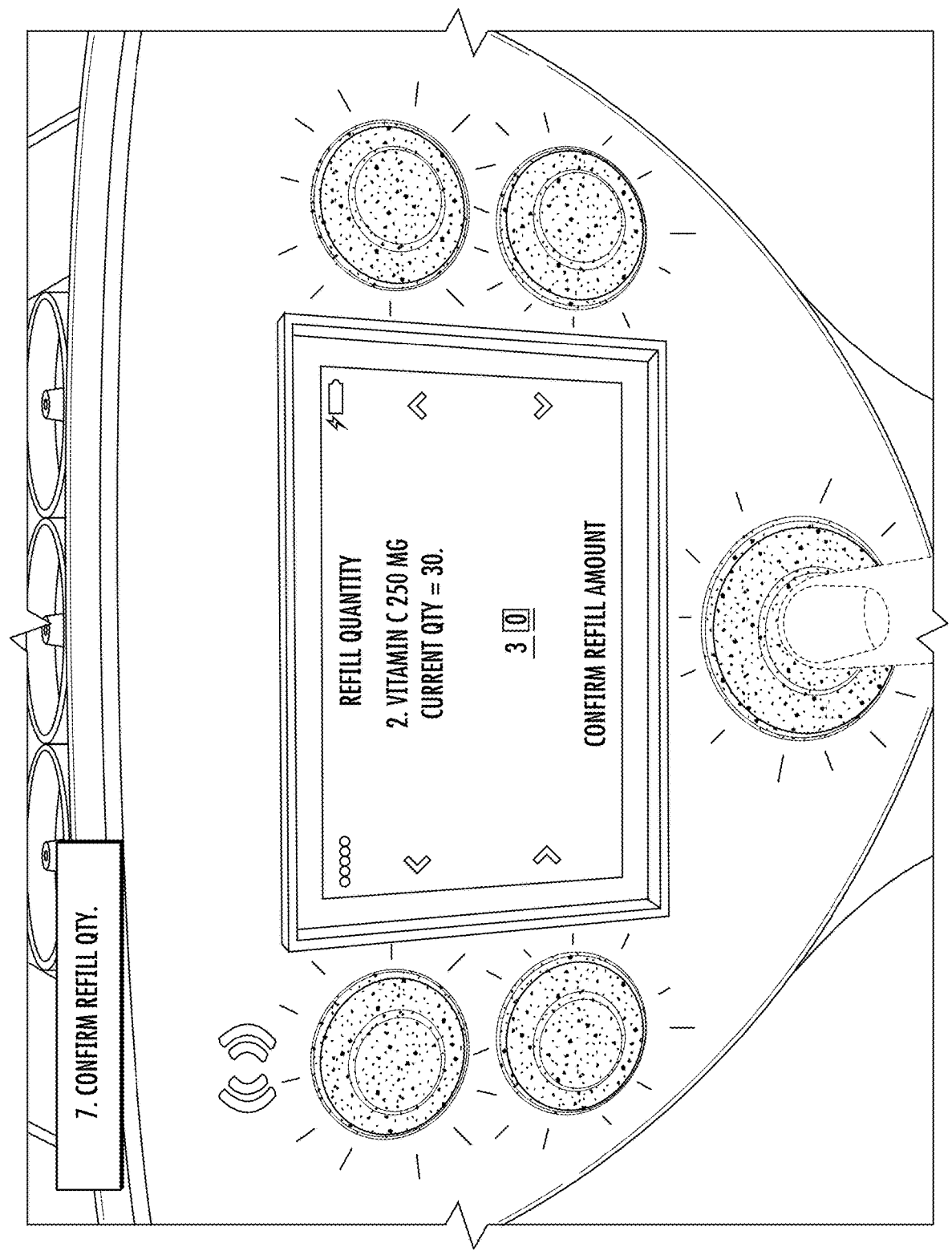
Figure 17:
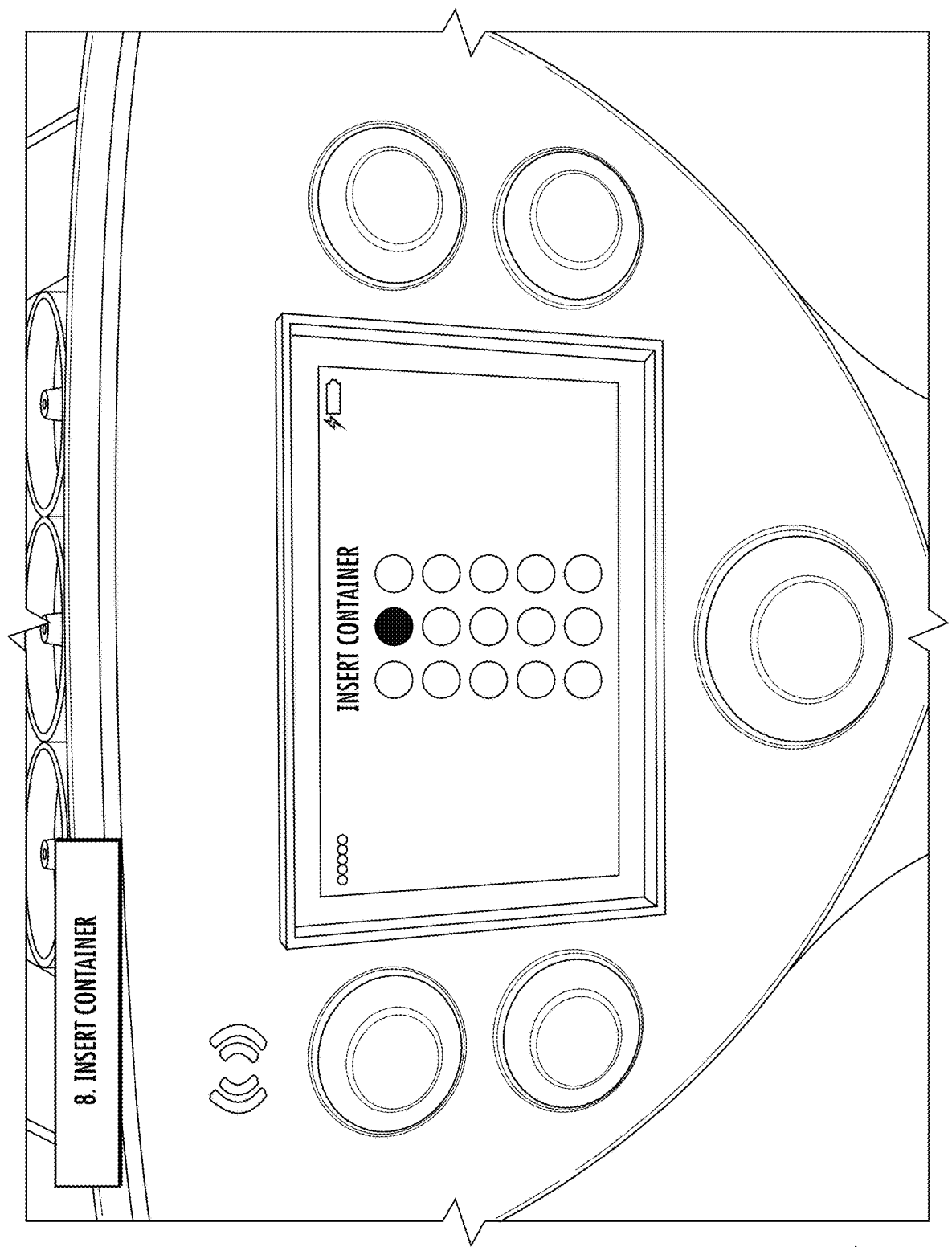
Figure 18:
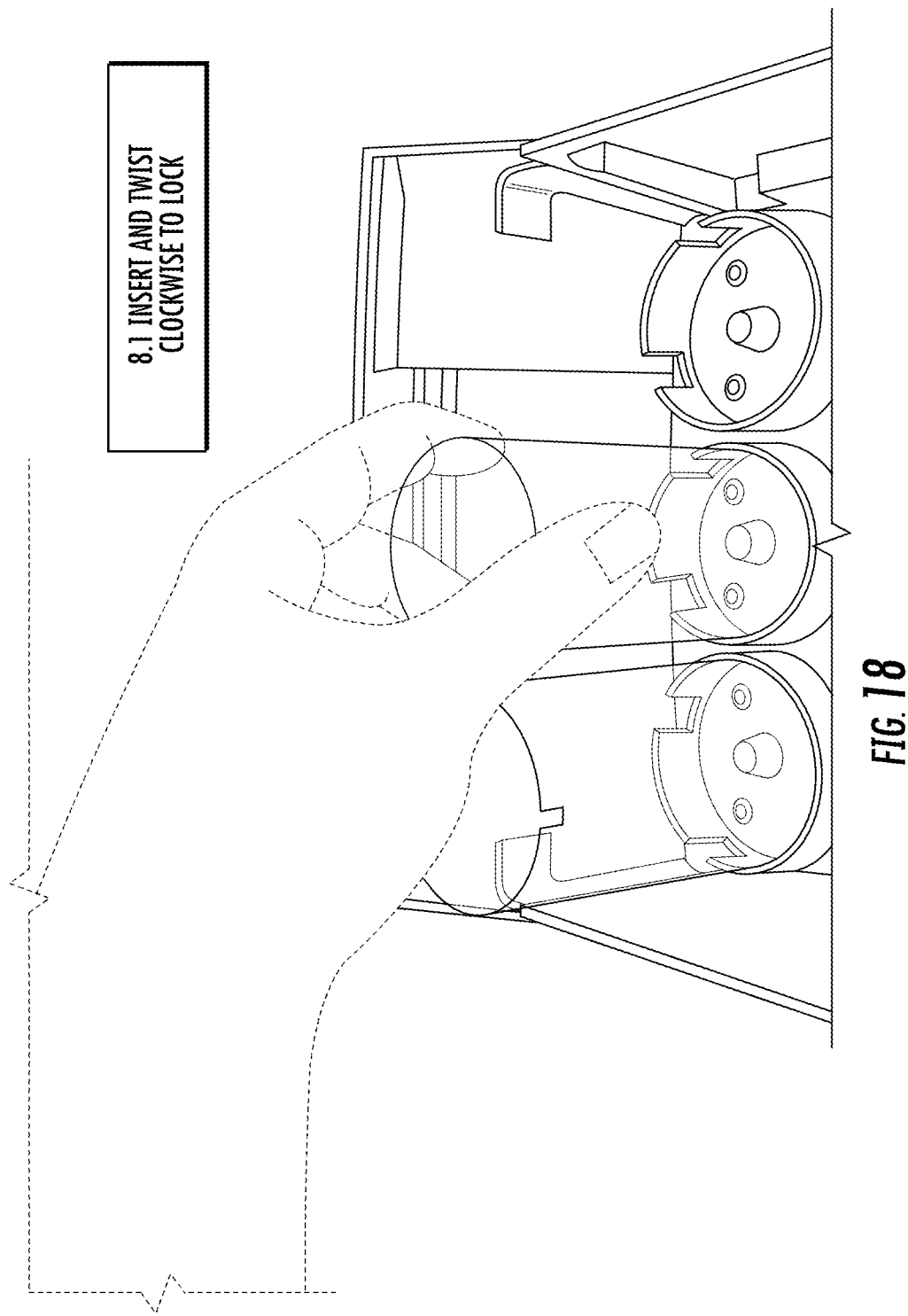
Figure 19:
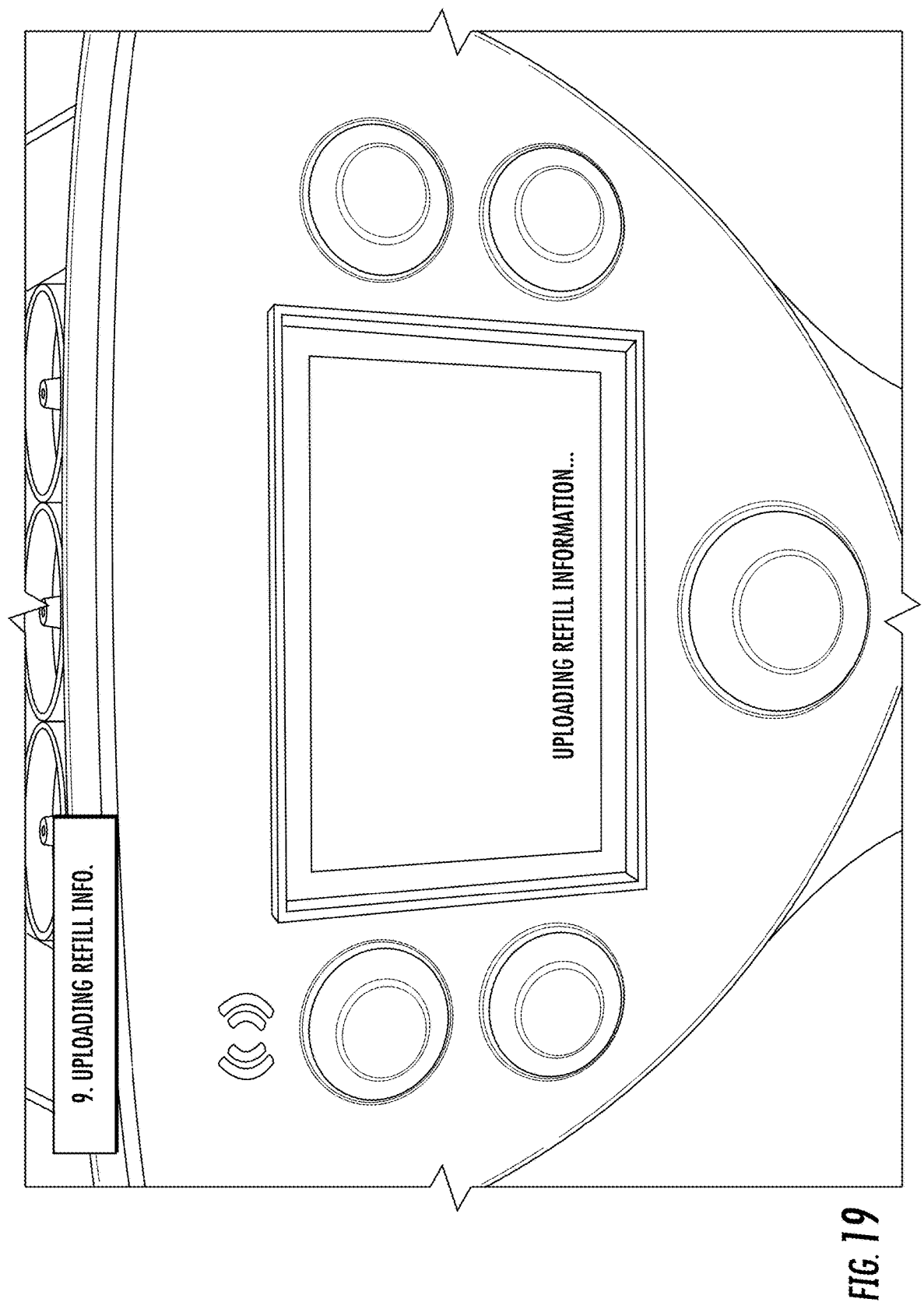
Figure 20:
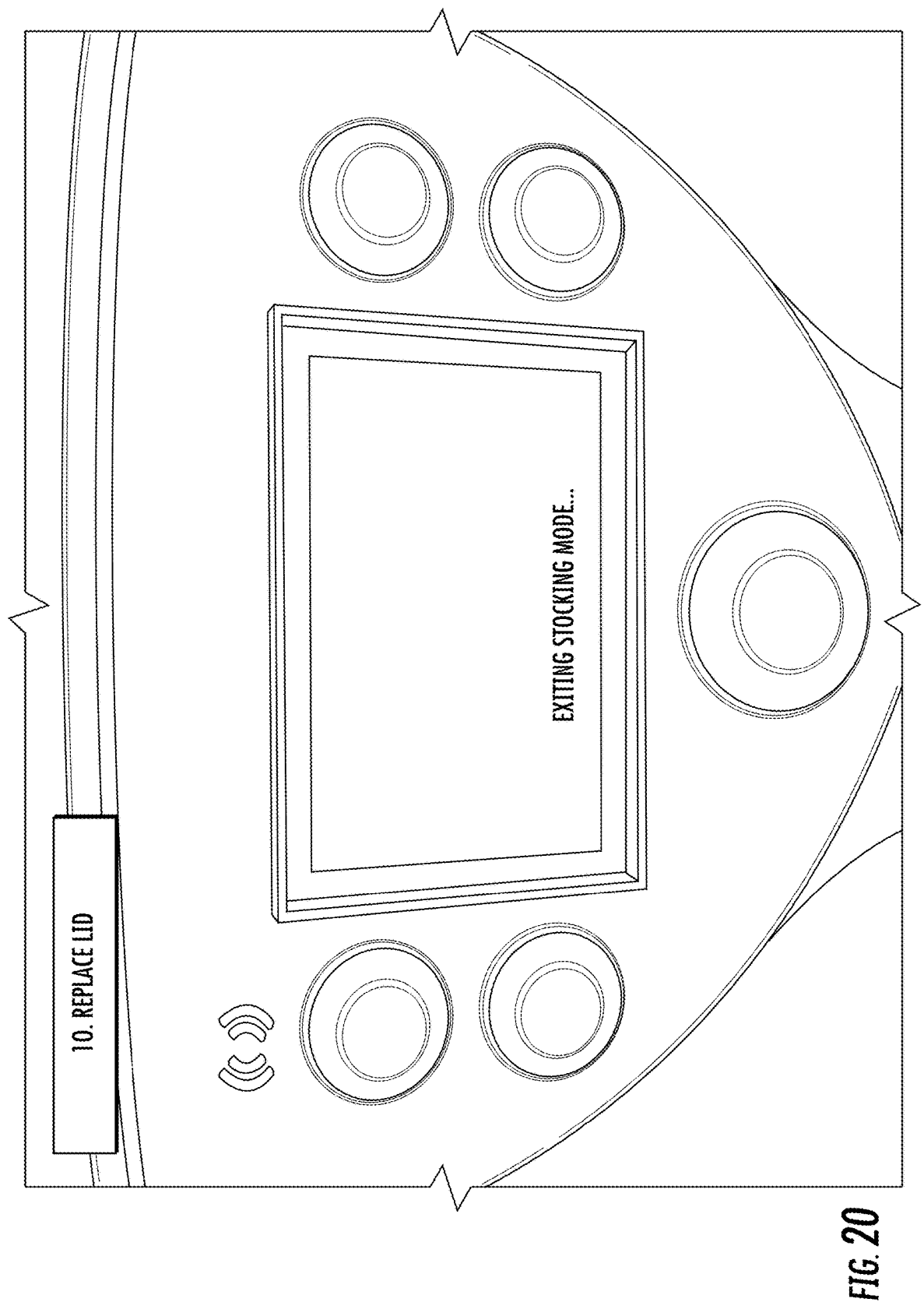
Figure 21:
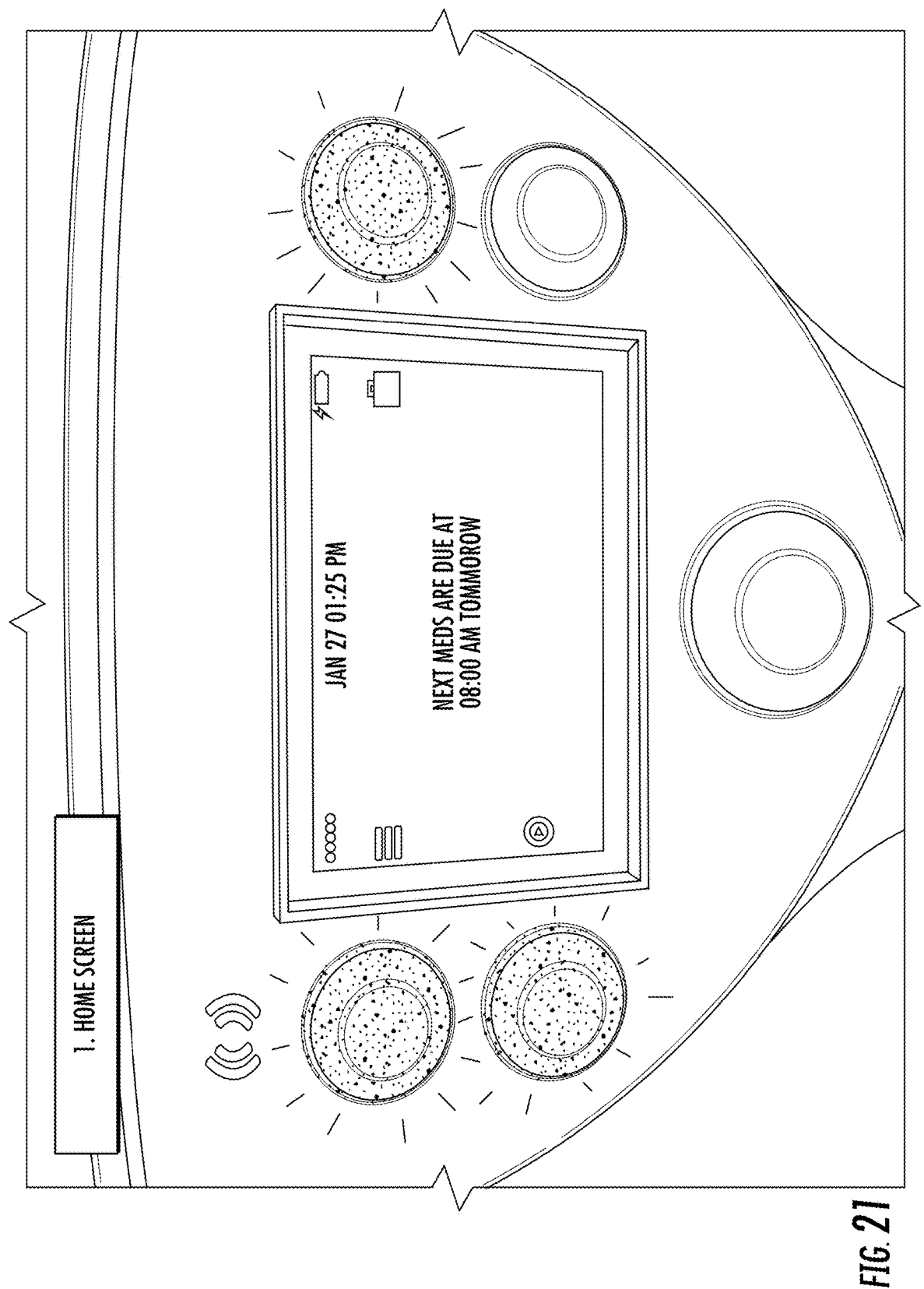
FIGS. 21 through 38 show a display of the dispensing apparatus of FIG. 1 performing a travel pack dispensing method in accordance with FIG. 8, with illuminated buttons in various of the figures being shown by rays and stippling.
Figure 22:
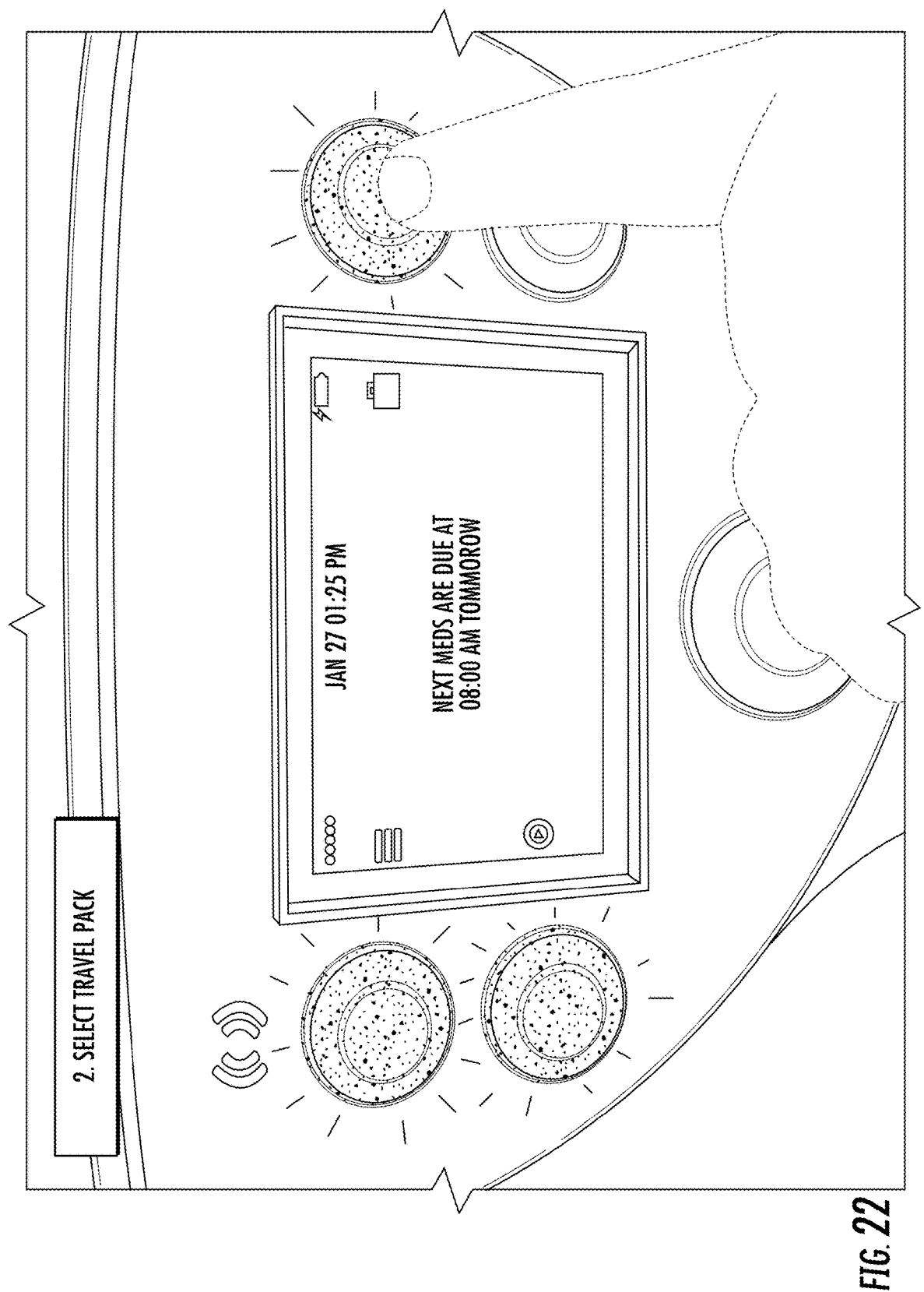
Figure 23:
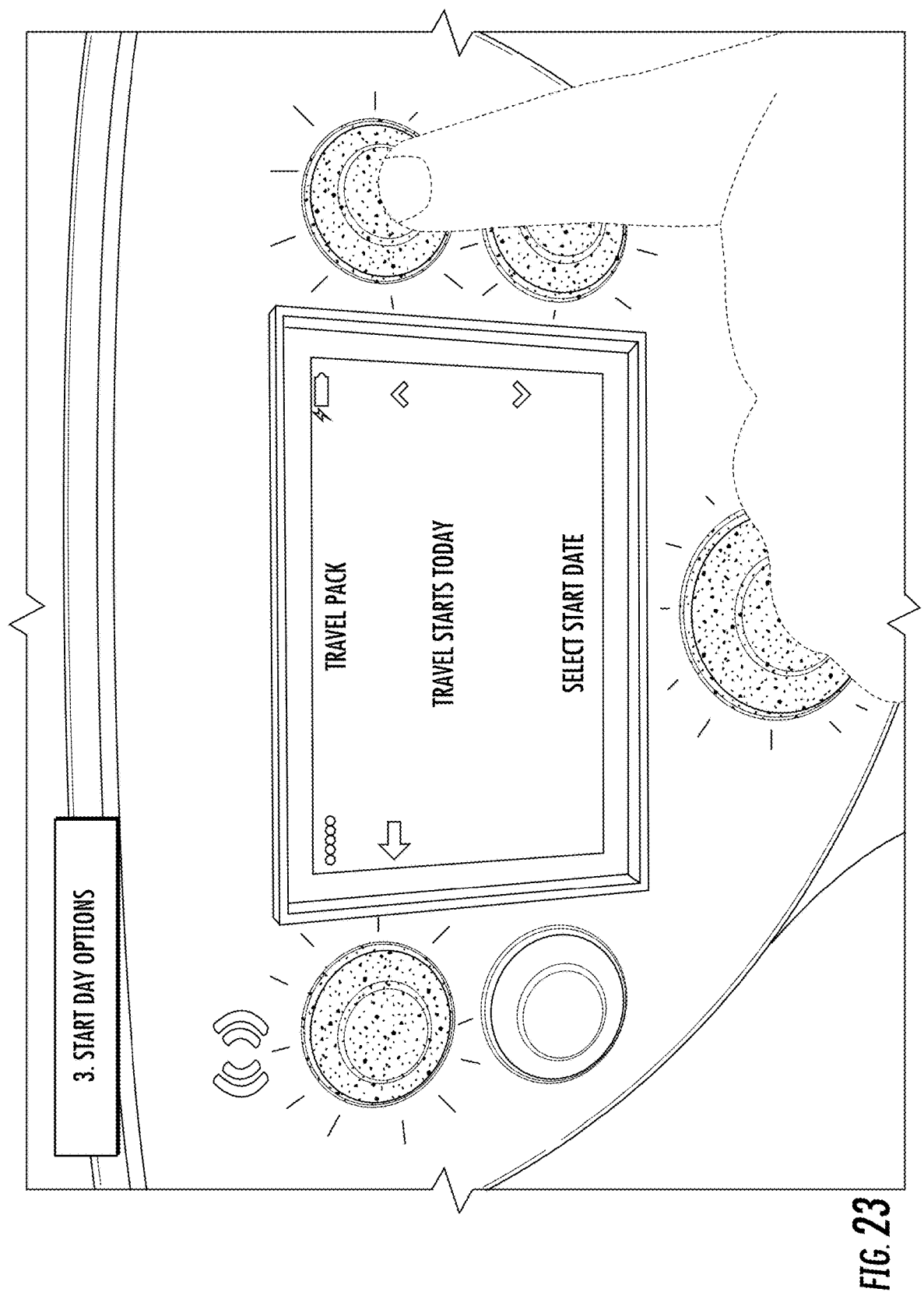
Figure 24:
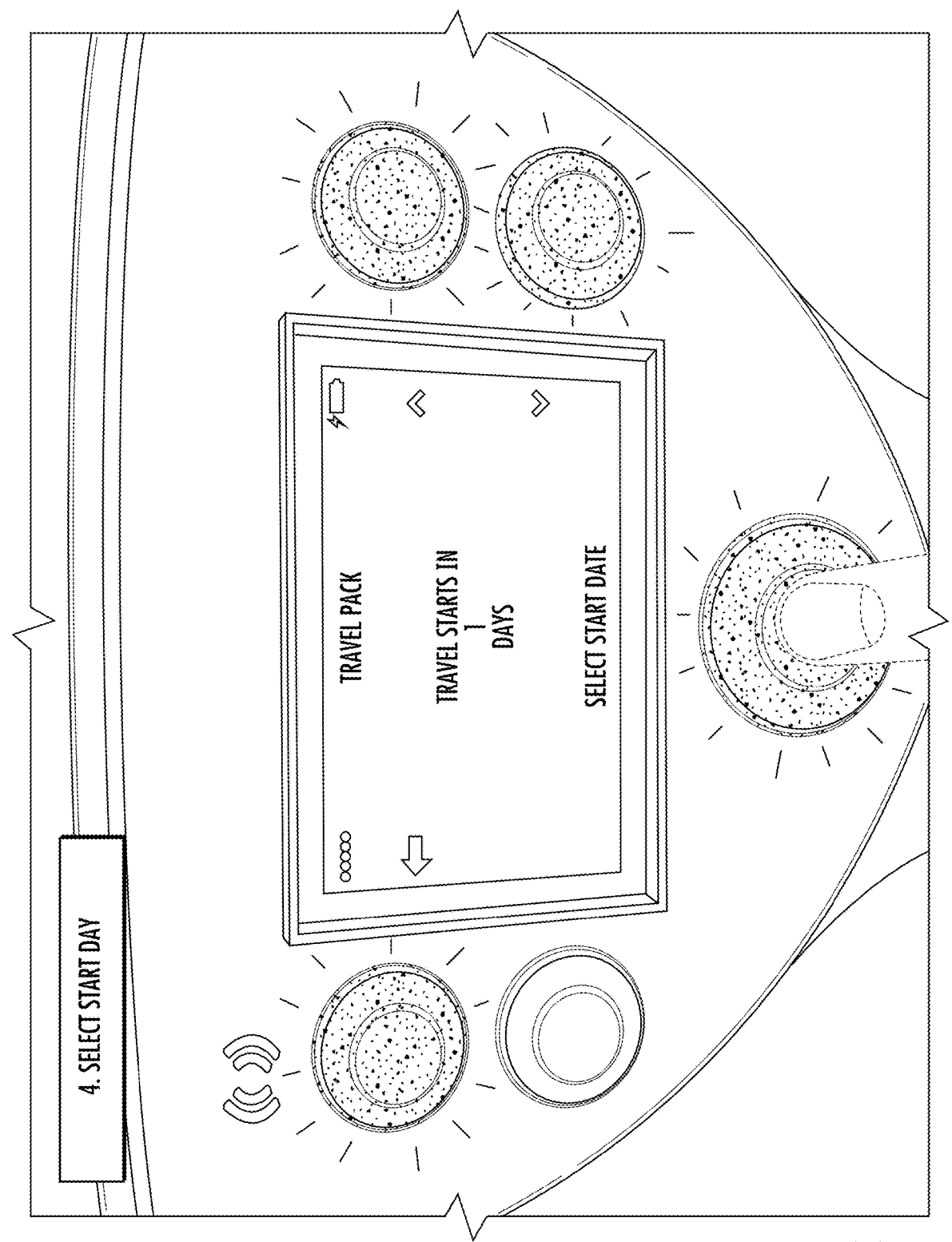
Figure 25:
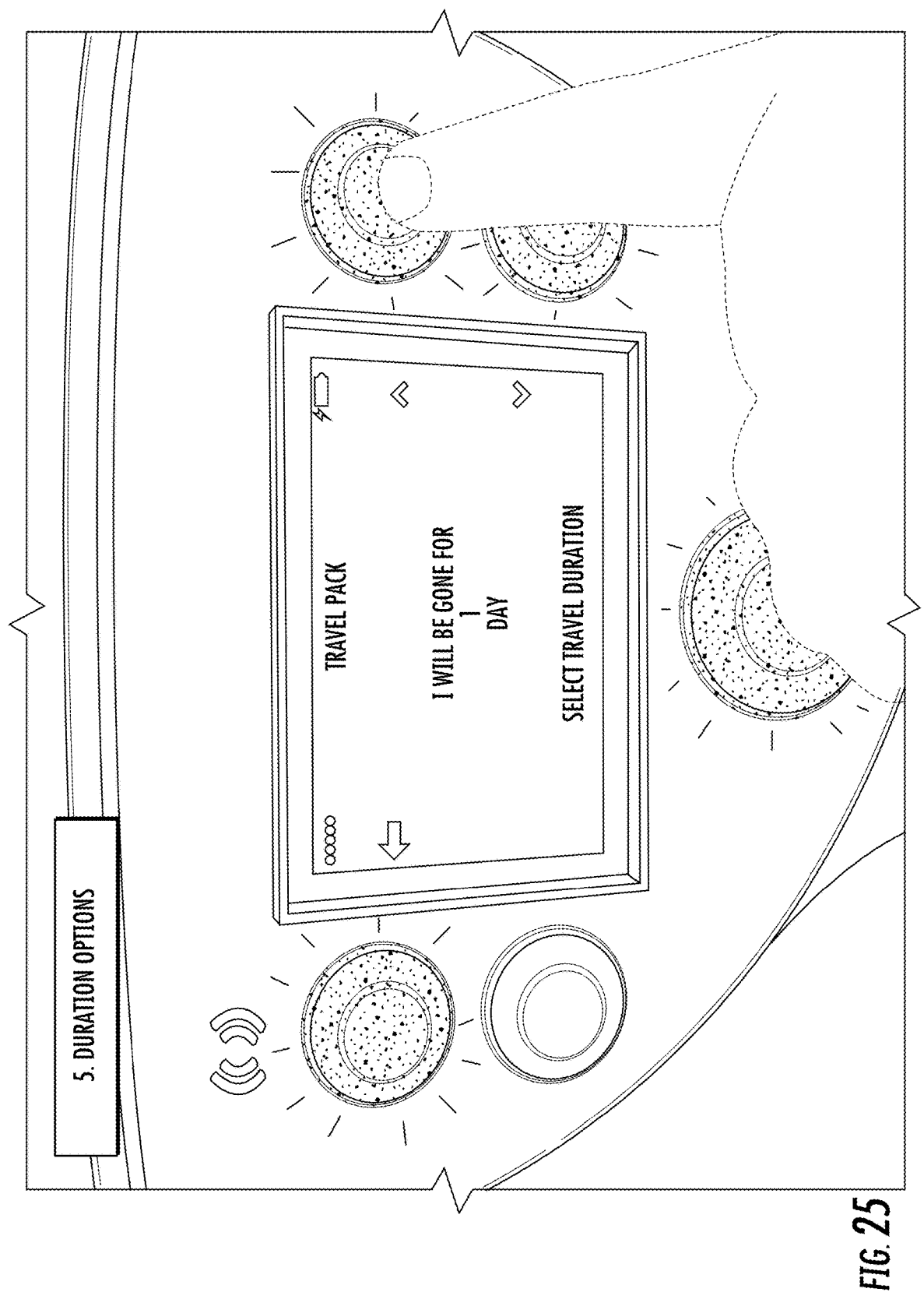
Figure 26:
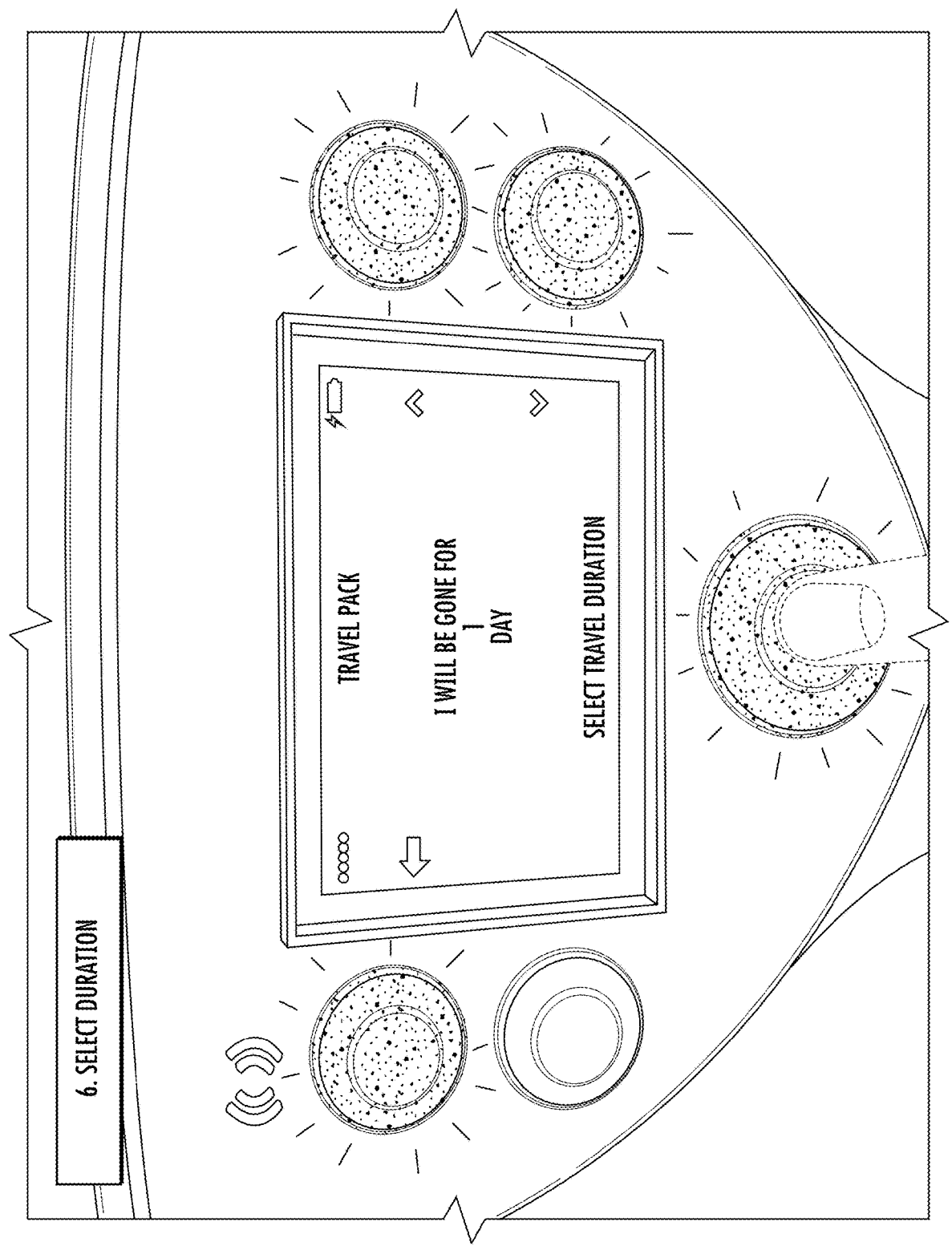
Figure 27:
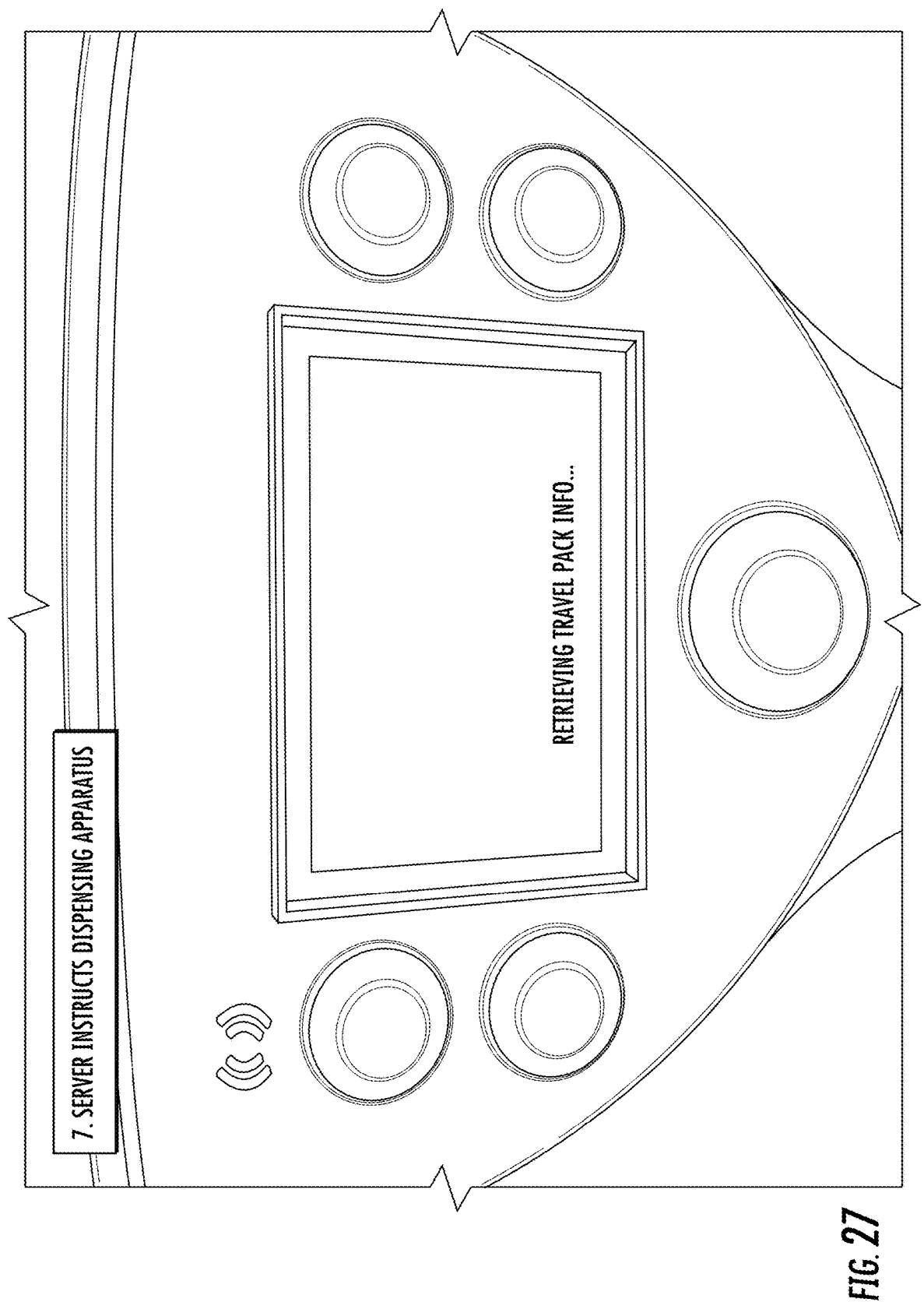
Figure 28:
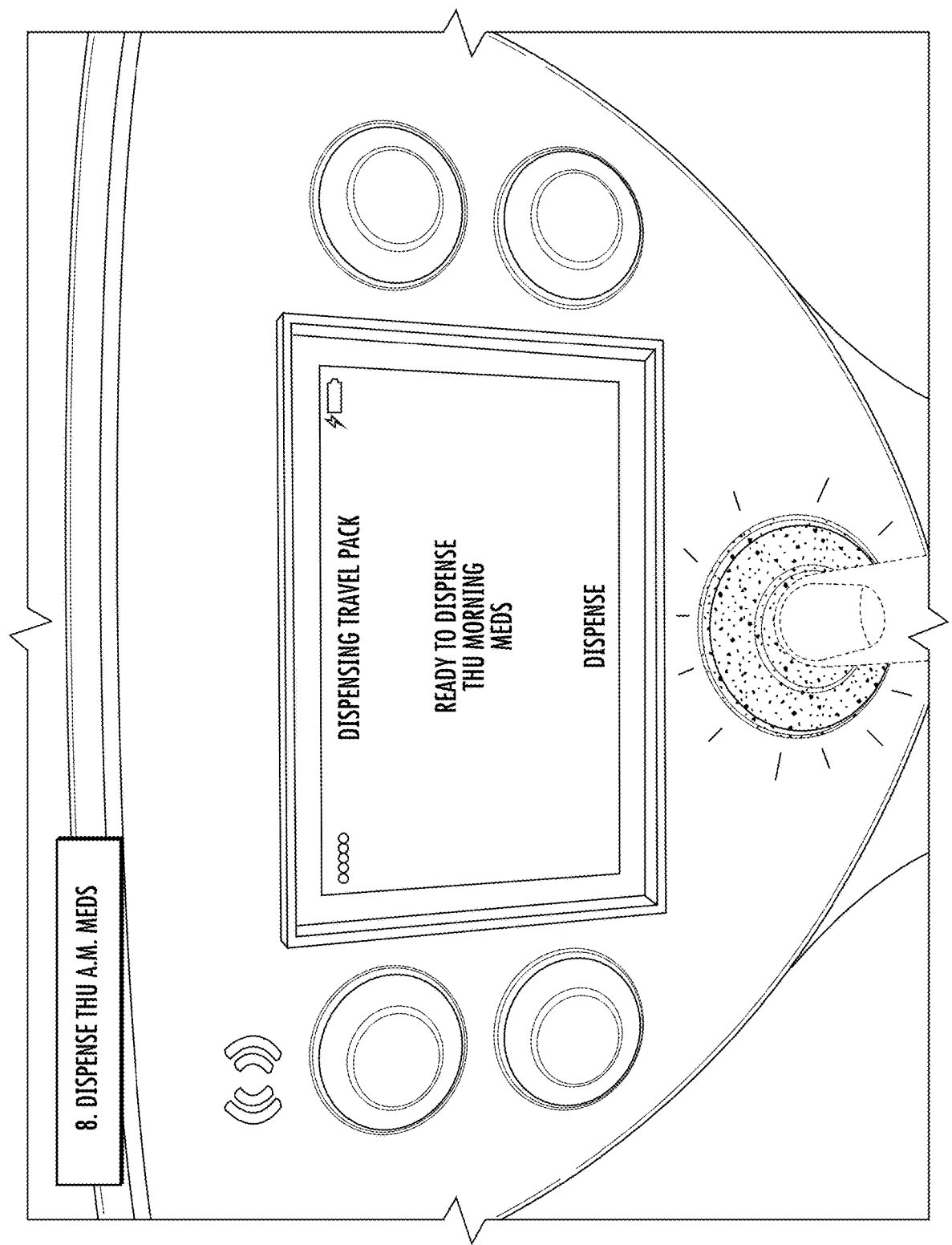
Figure 29:
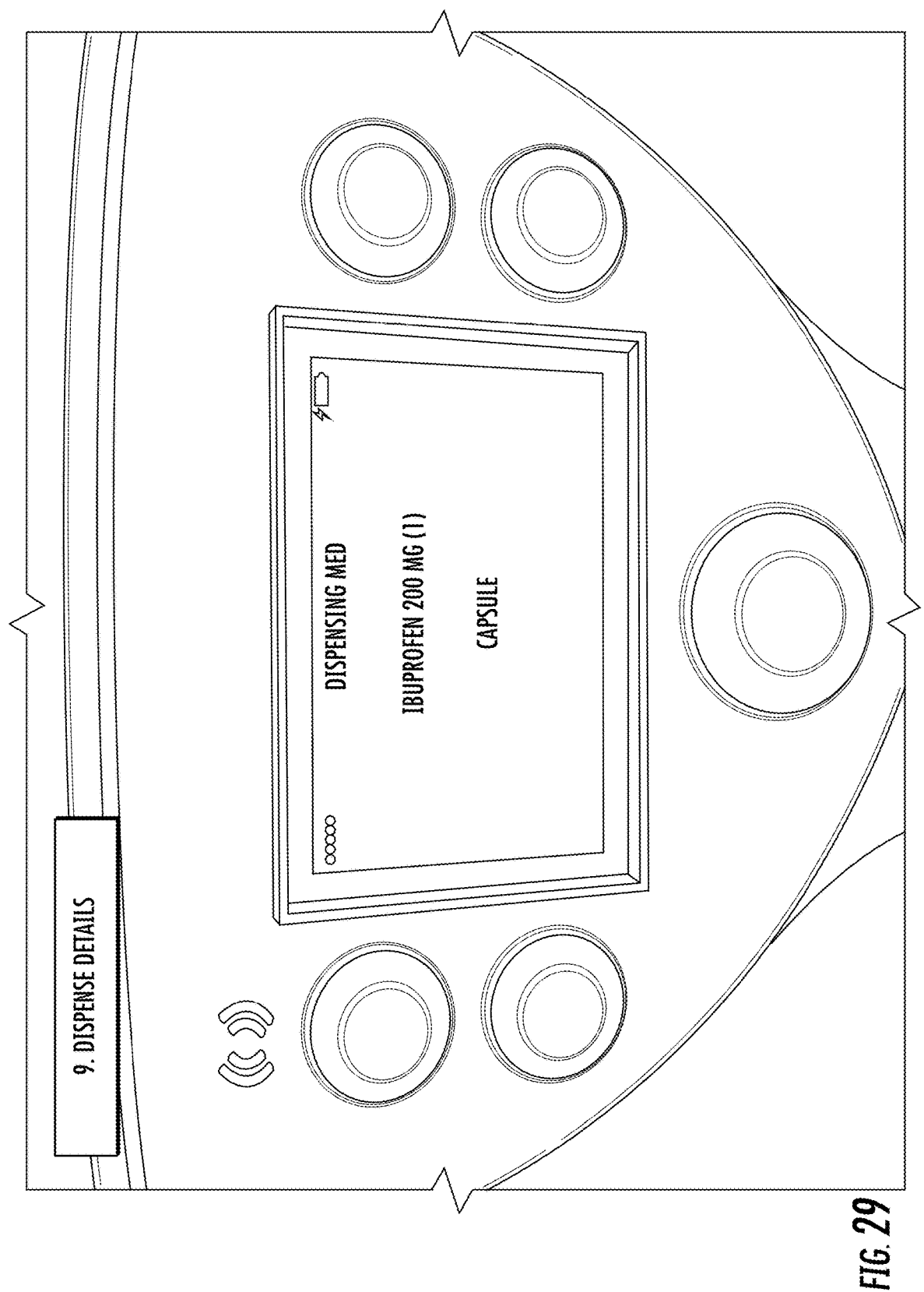
Figure 30:
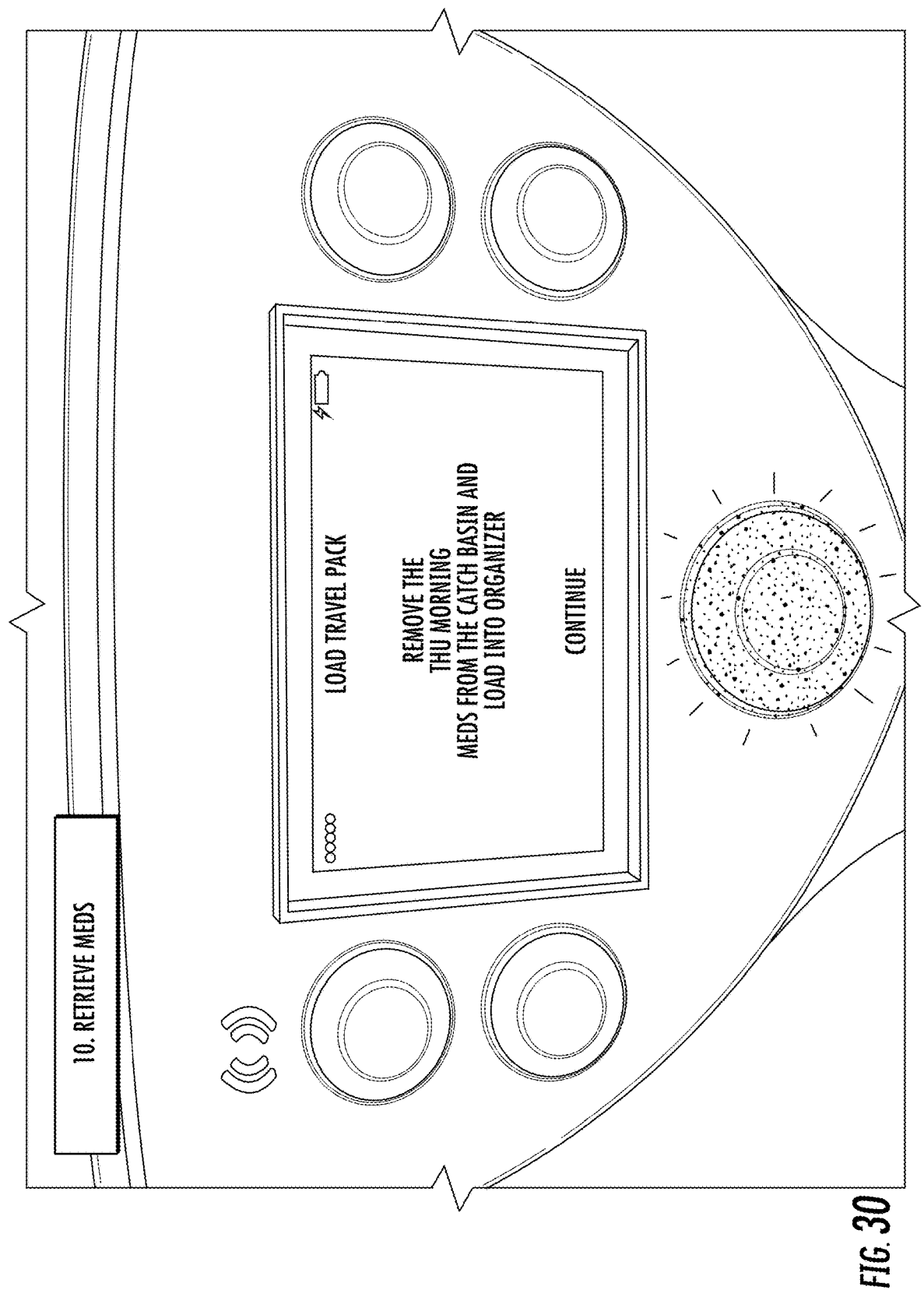
Figure 31:
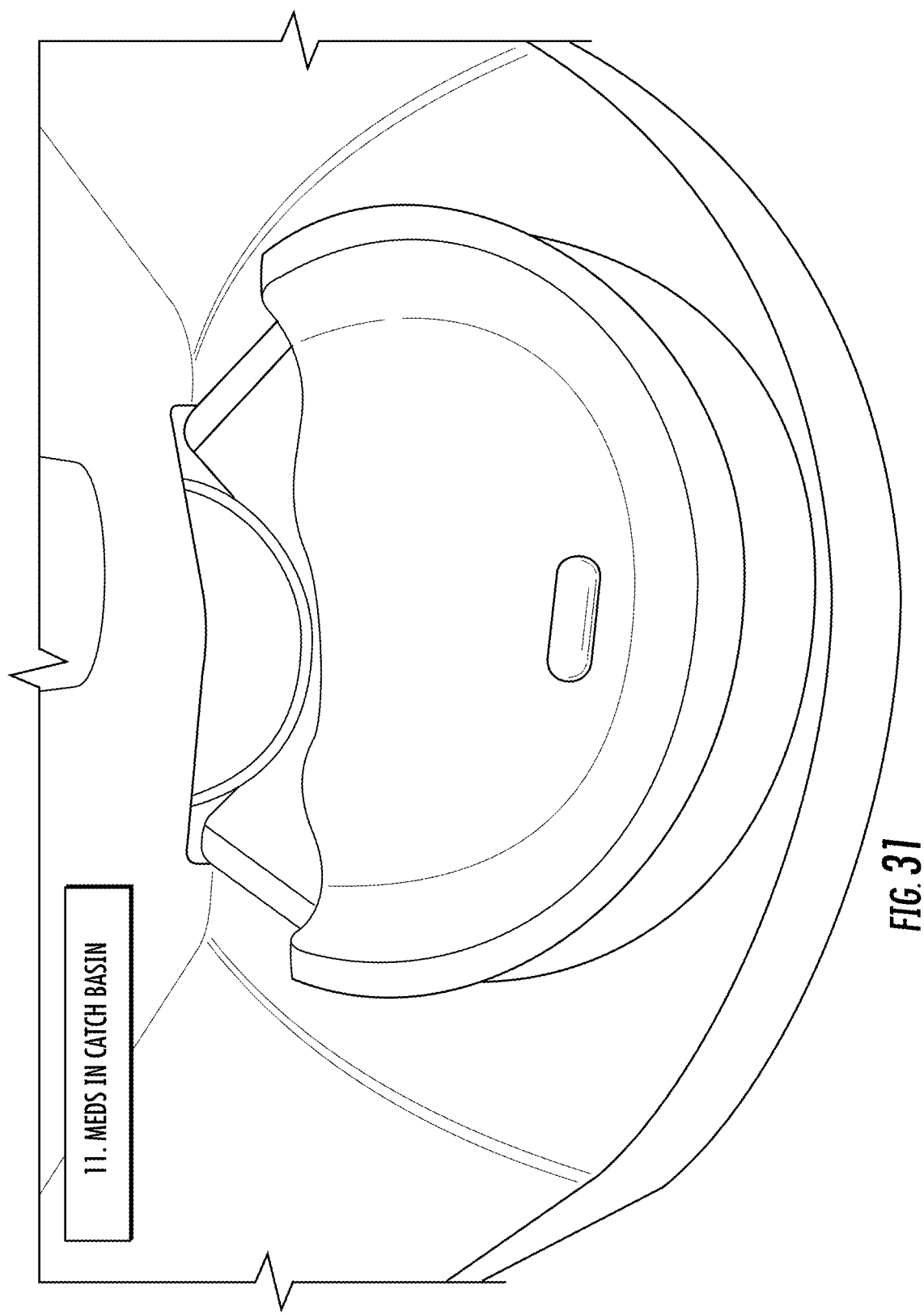
Figure 32:
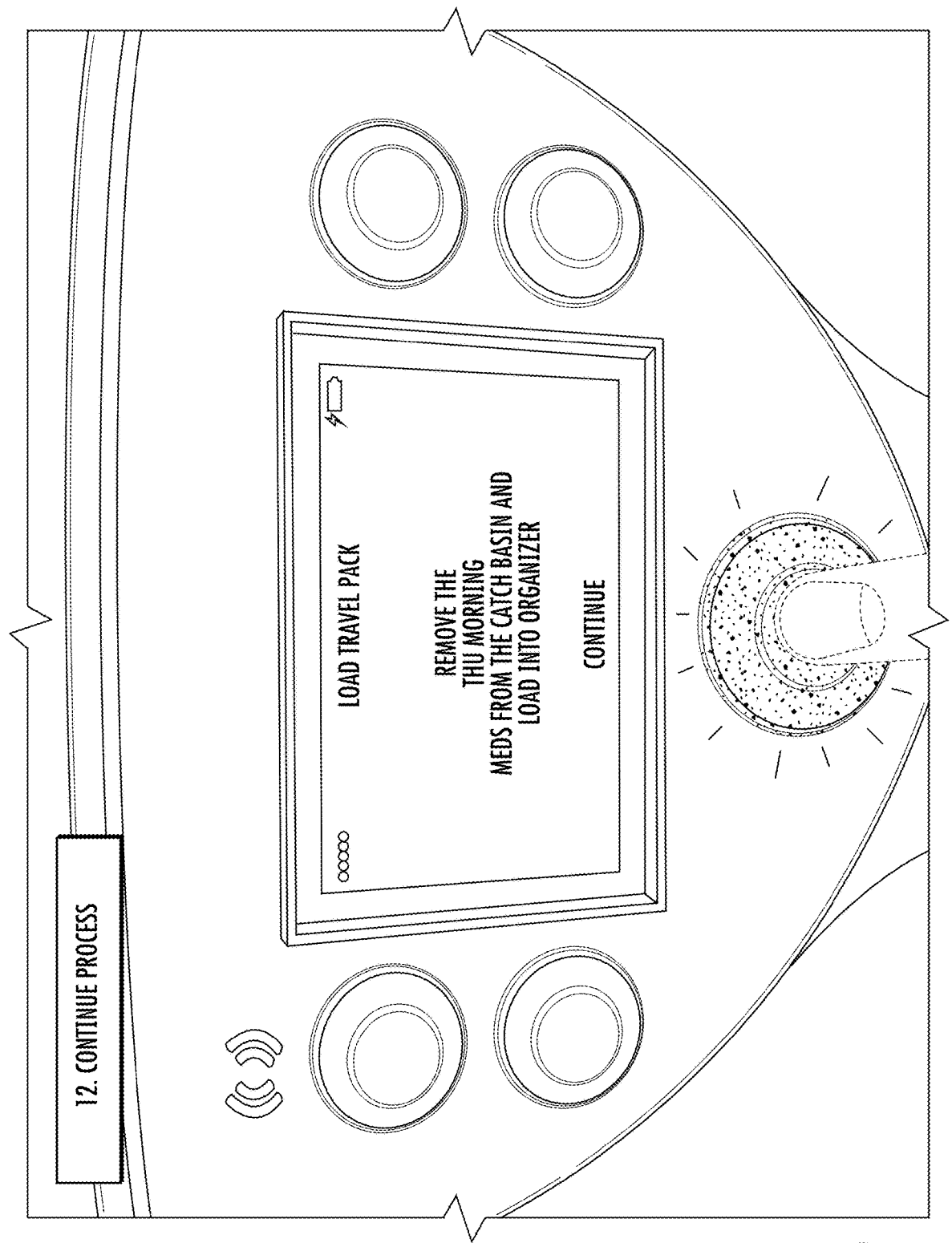
Figure 33:
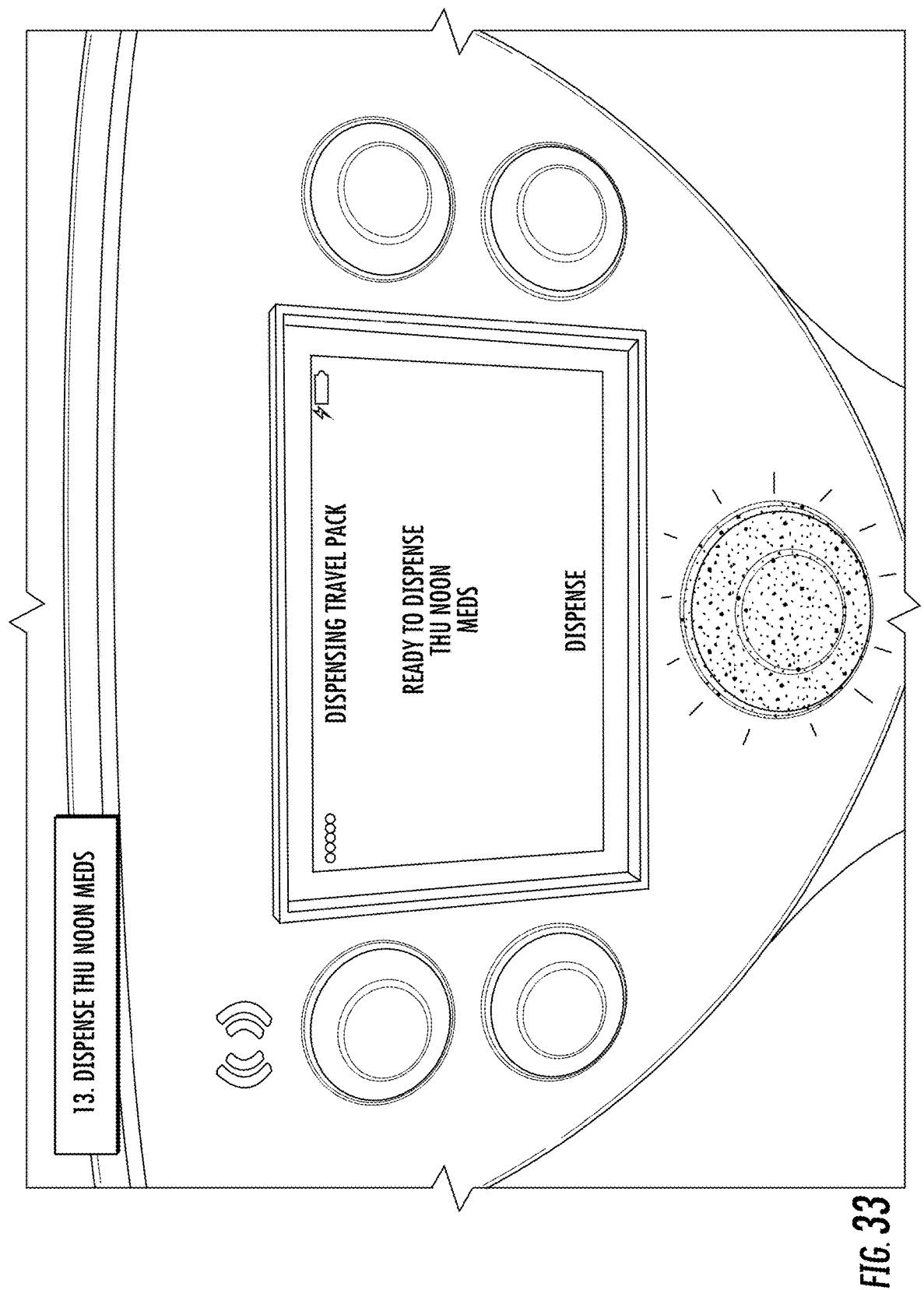
Figure 34:
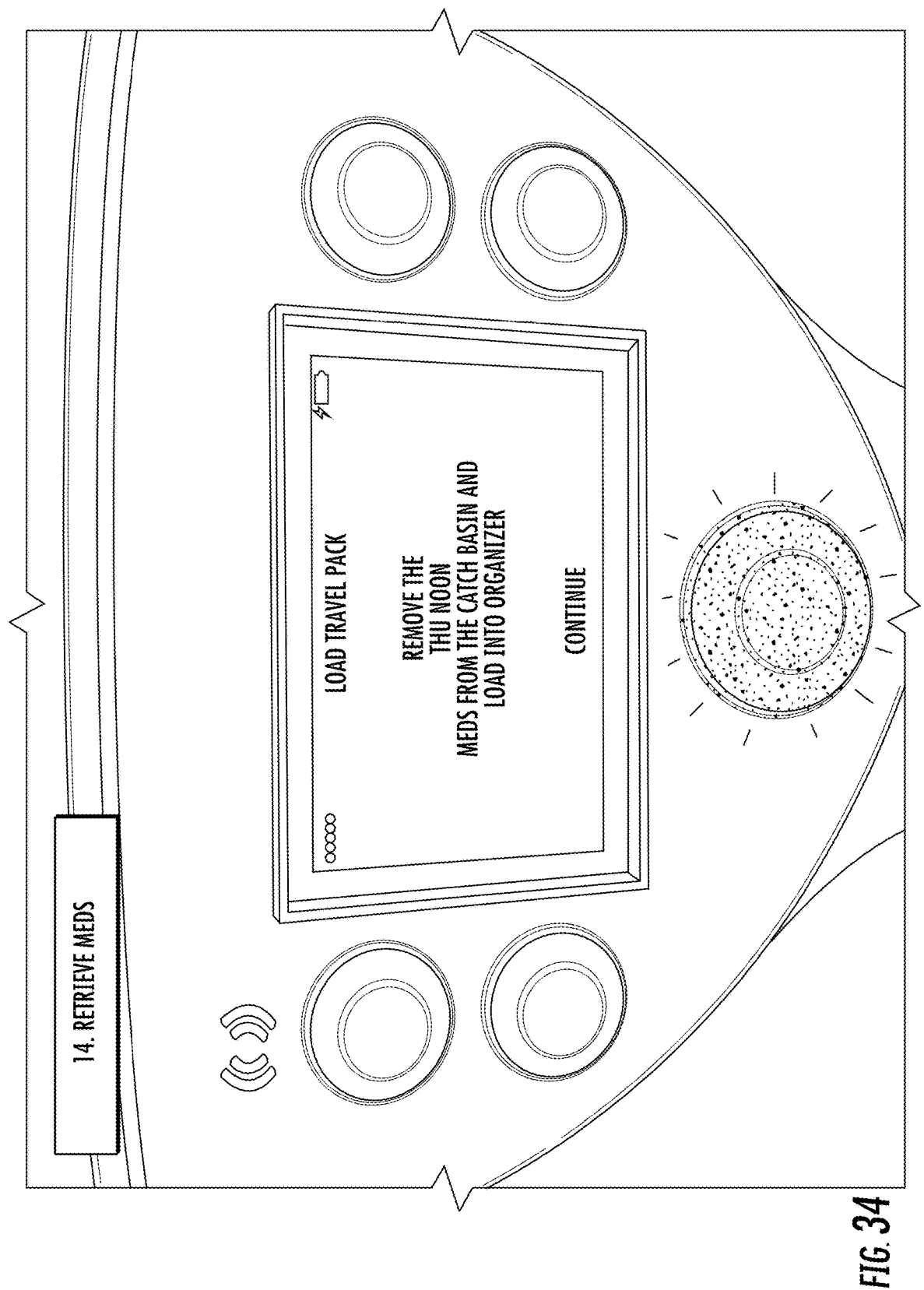
Figure 35:
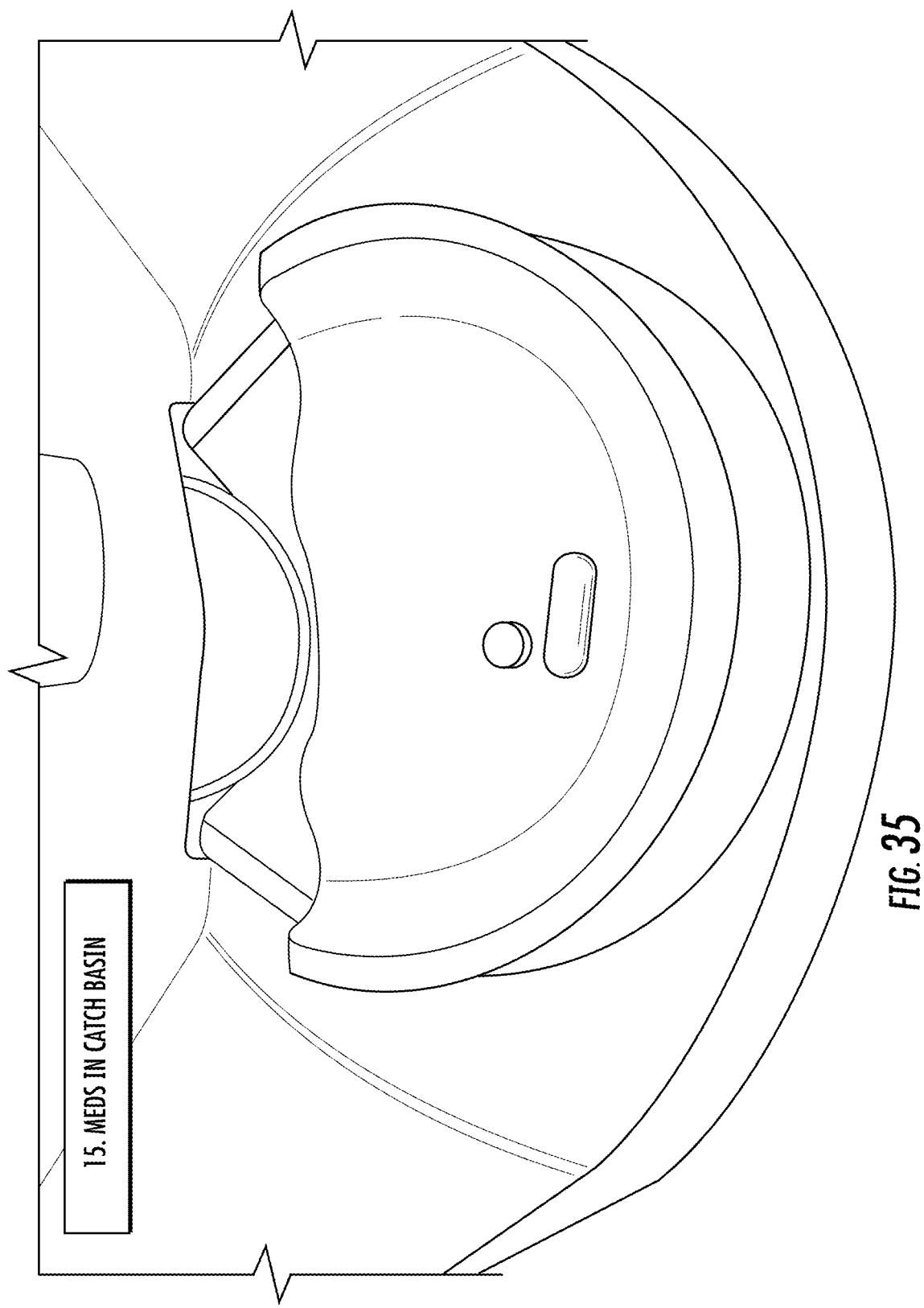
Figure 36:
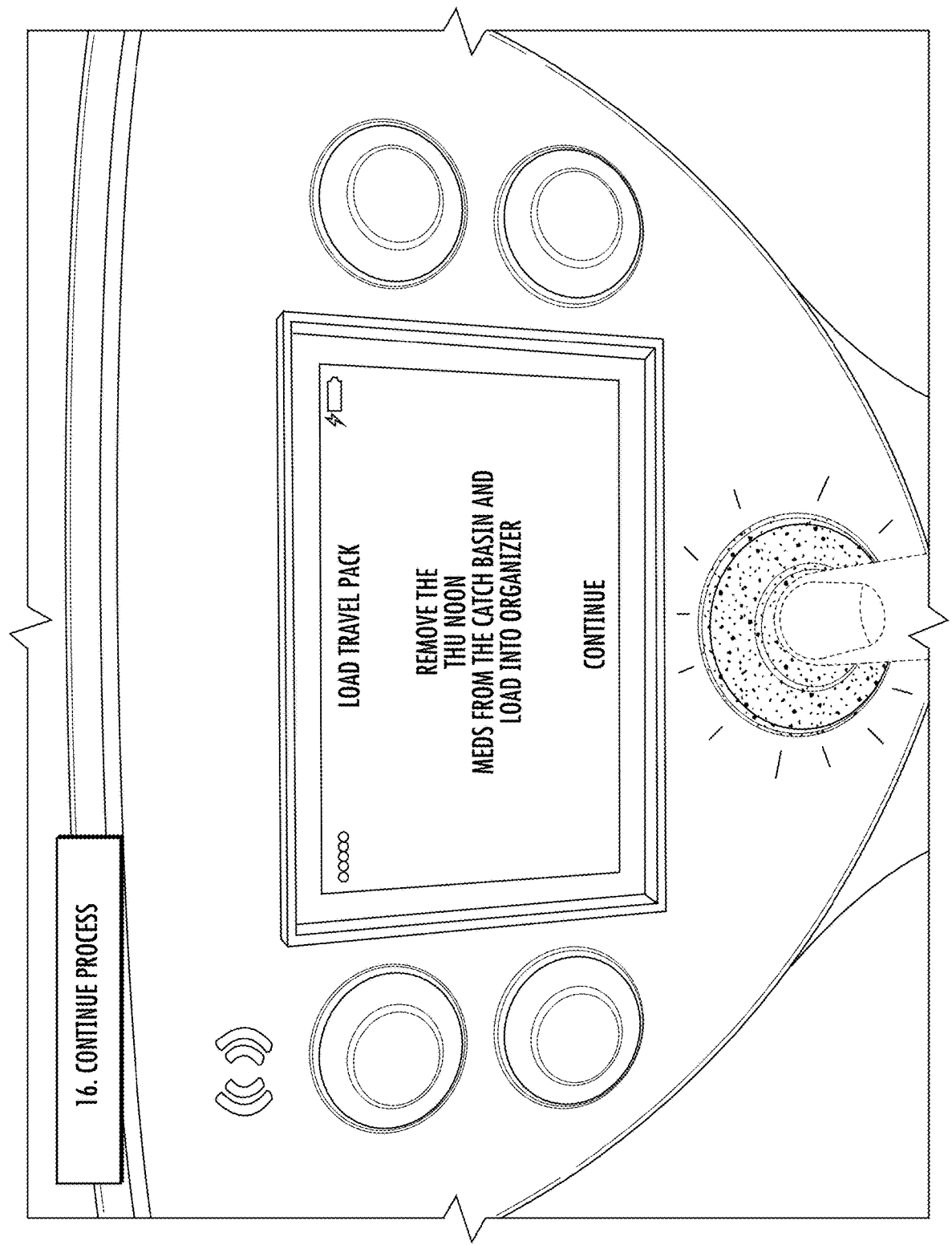
Figure 37:
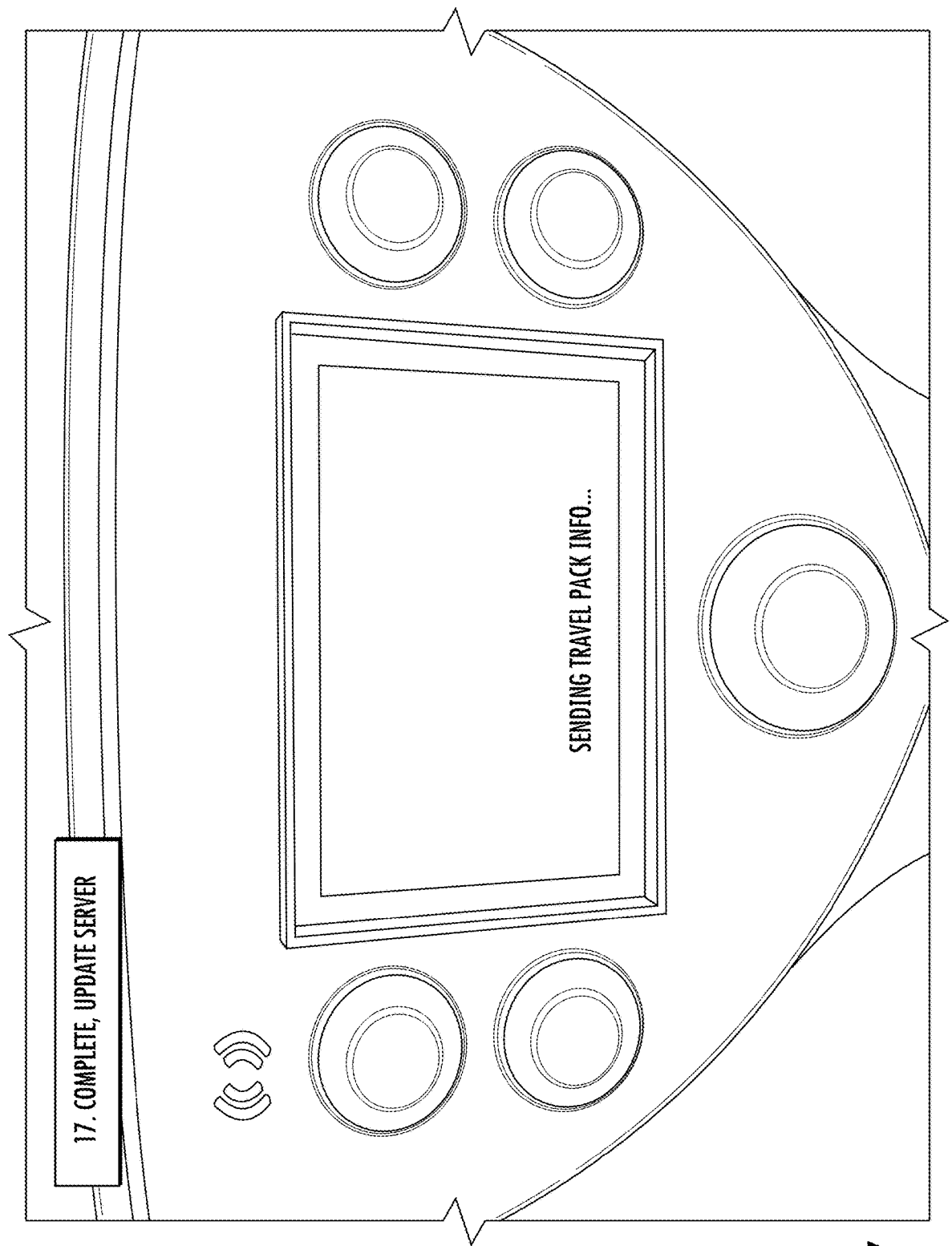
Figure 38:
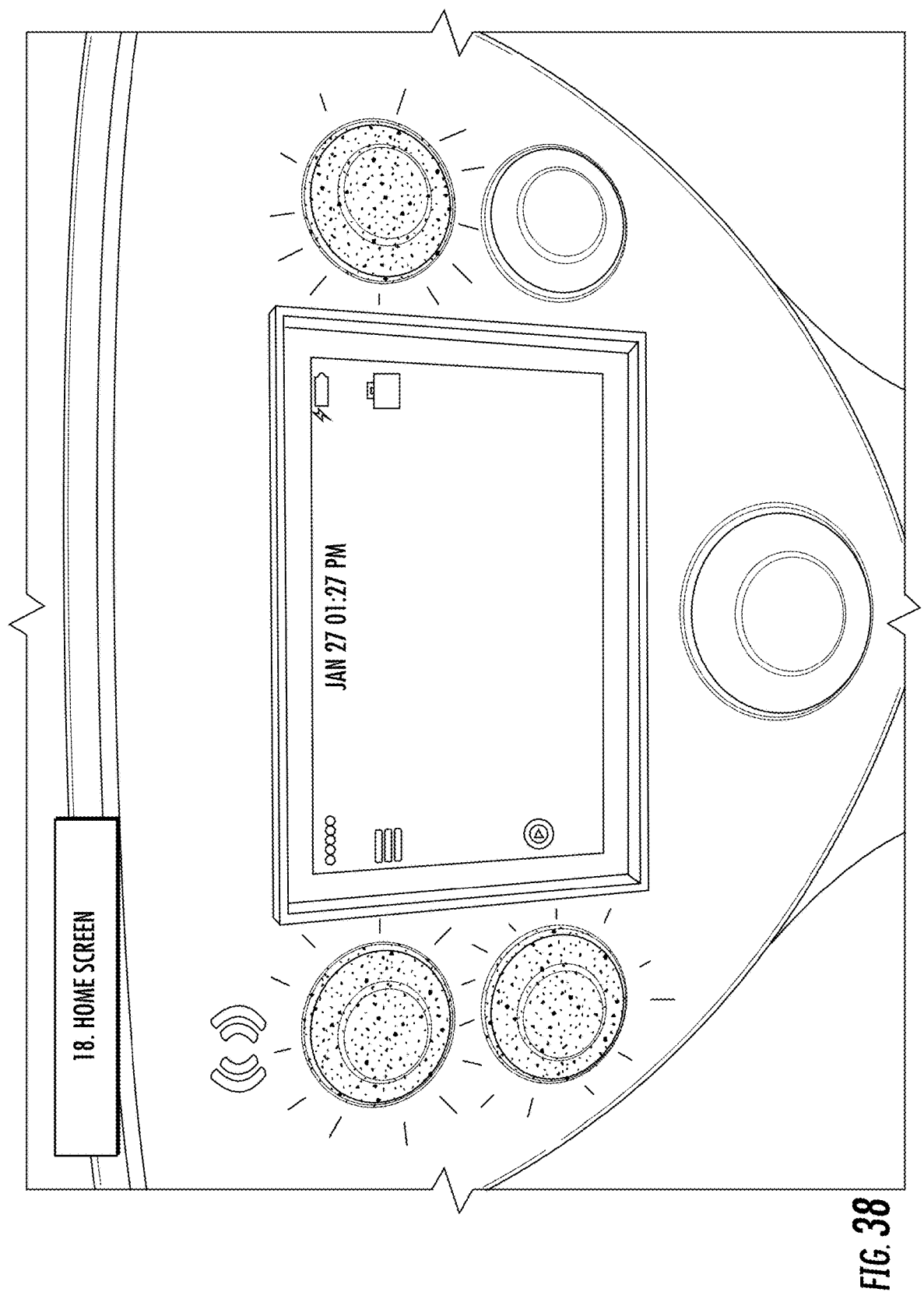

Referring now to FIG. 8, apparatus 10 preferably also accounts for times when the patient may be away for one or more days. In these situations, the individual (or his or her caregiver) may stock a "travel pack" that will accompany the patient during the period of absence. Typically, such travel packs are organized into four doses each day—morning, afternoon, night, and PRN (as needed). A particular slot in the travel pack, such as the morning slot, may contain more than one type of medicine if they are all to be taken together at the same time. Because apparatus 10 (and/or host server 54) "knows" the patient's prescription, travel pack stocking can be facilitated.

The process begins in this case at 800. The caregiver (or patient as the case may be) then selects the travel pack option using the menu on display 12. For example, in some embodiments, the default menu on display 12 may include an icon (such as a suitcase icon) indicating travel pack mode. After selecting the travel pack icon, the start date of travel and the number of days that the patient will be away are selected (at 804 and 806, respectively).

The "load out" based on the number of days is then determined by apparatus 10, or apparatus 10 obtains this information (at 808) from host server 54. Next, the load out for the away period is dispensed (at 810). Preferably, all dosages that the patient may need for each time are dispensed together so that the travel pack can be most efficiently stocked. For example, all medicines needed for the morning of the first day are dispensed before the medicines needed for the afternoon of the first day, etc. The travel pack is thus stocked sequentially, and acknowledged, before the next group of dosages is dispensed.

After the load out is finished, a report is made to host server 54 (at 812) and the inventory of apparatus 10 is decremented (at 814). Preferably, apparatus 10 is "locked" (at 816) such that it will not dispense during the travel pack period. Process ends at 818.

FIGS. 21-38 show an exemplary display sequence that might be seen on display 12 during travel pack stocking in accordance with the methodology of FIG. 8. These screen displays are believed to be self-explanatory, when considered in light of the above discussion, and need not be further discussed.

It can thus be seen that the present invention provides various novel aspects regarding a pharmaceutical dispenser. While preferred embodiments of the invention have been shown and described, modifications and variations may be made thereto by those of ordinary skill in the art without departing from the spirit and scope of the present invention. In addition, it should be understood that aspects of the various embodiments may be interchanged both in whole or in part to yield still further embodiments. Furthermore, those of ordinary skill in the art will appreciate that the foregoing description is by way of example only, and is not intended to be limitative of the invention as further described in the appended claims.

What is claimed is:

1. A solid dosage dispensing apparatus comprising:
a user interface including a display;
a coupling structure configured to mount a plurality of containers from which solid dosages are dispensed while mounted to the coupling structure; and
a controller operative during a stocking mode to:
(i) present on said display a list of different solid dosage types available for stocking;
(ii) receive an indication of a selected solid dosage type based on the list;
(iii) graphically indicate on said display a container location at which the selected solid dosage type is to be located; and
(iv) confirm container removal from the container location and subsequent container replacement in that location.

2. A solid dosage dispensing apparatus as set forth in claim 1, wherein said controller is further operative to provide an alarm if a container is placed in an incorrect location.

3. A solid dosage dispensing apparatus as set forth in claim 1, wherein said controller prompts a user to confirm a number of the selected solid dosage type to be added.

4. A solid dosage dispensing apparatus as set forth in claim 3, wherein the number of the selected solid dosage type can be varied by the user via the user interface.

5. A solid dosage dispensing apparatus as set forth in claim 1, further comprising communication circuitry operative to communicate with a remote host server.

6. A solid dosage dispensing apparatus as set forth in claim 5, wherein said communication circuitry is operative to communicate with the remote host server via internet connection.

7. A solid dosage dispensing apparatus as set forth in claim 5, wherein said communication circuitry is operative to communicate with the remote host server via cellular connection.

8. A solid dosage dispensing apparatus as set forth in claim 5, wherein said controller is operative to update an inventory of the selected solid dosage type with the remote host server via said communication circuitry.

9. A solid dosage dispensing apparatus as set forth in claim 1, further comprising a readable indicia reader.

10. A solid dosage dispensing apparatus as set forth in claim 9, wherein said controller is operative to receive information via said readable indicia reader regarding the selected solid dosage type and quantity thereof.

11. A solid dosage dispensing apparatus as set forth in claim 9, wherein said readable indicia reader comprises a RFID unit.

12. A method implemented by a solid dosage dispensing apparatus which dispenses dosages from a plurality of containers mounted in a housing of the dispensing apparatus, said method comprising steps of:
(a) receiving a request to enter into a stocking mode;
(b) graphically displaying a list of dosage types to be stocked;
(c) receiving an indication of a selected dosage type based on the list;
(d) based on said selected dosage type, indicating a container location on a display of said dispensing apparatus; and
(e) electronically confirming container removal from the container location and subsequent container replacement in that location.

13. A solid dosage dispensing apparatus comprising:
a user interface including a display;
a plurality of containers from which solid dosages are dispensed; and
a controller operative during a stocking mode to:
(i) present on said display a list of different solid dosage types available for stocking;
(ii) receive an indication of a selected solid dosage type;
(iii) graphically indicate on said display a container location at which the selected solid dosage type is to be located; and
(iv) confirm container removal from the container location and subsequent container replacement in that location,
wherein said apparatus comprises a lid and said controller enters the stocking mode upon removal of the lid.

* * * * *